(12) United States Patent
Koh et al.

(10) Patent No.: US 11,046,779 B2
(45) Date of Patent: Jun. 29, 2021

(54) ANTIBODY SPECIFICALLY BINDING TO PAUF PROTEIN AND USE THEREOF

(71) Applicants: DONG-A UNIVERSITY RESEARCH FOUNDATION FOR INDUSTRY-ACADEMY COOPERATION, Busan (KR); PRESTIGE BIOPHARMA PTE. LTD., Singapore (SG)

(72) Inventors: Sang Seok Koh, Busan (KR); Yeon Jeong Kim, Busan (KR); So Eun Youn, Gyeongsangbuk-do (KR); Song Cheol Kim, Seoul (KR); Seung-Mo Hong, Seoul (KR); Seong Yun Jeong, Gyeonggi-do (KR)

(73) Assignees: DONG-A UNIVERSITY RESEARCH FOUNDATION FOR INDUSTRY-ACADEMY COOPERATION, Busan (KR); PRESTIGE BIOPHARMA PTE. LTD., Singapore (SG)

( * ) Notice: Subject to any disclaimer, the term of this patent is extended or adjusted under 35 U.S.C. 154(b) by 77 days.

(21) Appl. No.: 16/346,928

(22) PCT Filed: Aug. 16, 2017

(86) PCT No.: PCT/KR2017/008893
§ 371 (c)(1),
(2) Date: May 2, 2019

(87) PCT Pub. No.: WO2019/022281
PCT Pub. Date: Jan. 31, 2019

(65) Prior Publication Data
US 2020/0055951 A1     Feb. 20, 2020

(30) Foreign Application Priority Data
Jul. 28, 2017 (KR) ........................ 10-2017-0096370

(51) Int. Cl.
*C07K 16/30*   (2006.01)
*A61K 47/68*   (2017.01)
*A61P 35/00*   (2006.01)
*A61K 39/00*   (2006.01)
*G01N 33/574*  (2006.01)

(52) U.S. Cl.
CPC ........ *C07K 16/303* (2013.01); *A61K 47/6851* (2017.08); *A61P 35/00* (2018.01); *G01N 33/574* (2013.01); *A61K 2039/505* (2013.01); *C07K 2317/24* (2013.01); *C07K 2317/565* (2013.01); *C07K 2317/567* (2013.01); *C07K 2317/73* (2013.01); *C07K 2317/92* (2013.01); *G01N 2500/10* (2013.01)

(58) Field of Classification Search
CPC .............. C07K 16/303; C07K 2317/24; C07K 2317/565; C07K 2317/567; C07K 2317/92; A61K 47/6851; A61K 2039/505; A61K 39/39558; A61P 35/00; G01N 2500/00

See application file for complete search history.

(56) References Cited

FOREIGN PATENT DOCUMENTS

| KR | 10-2011-0122807 A | 11/2011 |
| KR | 10-1098186 B1 | 12/2011 |
| KR | 10-1504039 B1 | 3/2015 |
| WO | WO 2007-145466 A1 | 12/2007 |
| WO | PCT-KR2017-008173 | 7/2017 |
| WO | WO 2019/022274 A1 | 1/2019 |

OTHER PUBLICATIONS

Kim et al., Biochemical and Biophysical Research Communications 454 (2014) 144-150. (Year: 2014).*
Kim, Sun A. et al., "Pancreatic Adenocarcinoma Up-regulated Factor (PAUF), a Novel Up-regulated Secretory Protein in Pancreatic Ductal Adenocarcinoma", Cancer Science, May 2009, vol. 100, No. 5, pp. 828-836.
Kim, Yun-Hee et al., "Efficient Targeting and Tumor Retardation Effect of Pancreatic Adenocarcinoma Up-regulated Factor (PAUF)-specific RNA Replacement in Pancreatic Cancer Mouse Model", Cancer Letters, 2014, vol. 344, pp. 223-231.
International Search Report dated Oct. 22, 2018 in connection with PCT International Application No. PCT/KR2017/008893.
Written Opinion (form PCT/ISA/237) dated Oct. 22, 2018 in connection with PCT International Application No. PCT/KR2017/008893.
Extended European Search Report dated Mar. 12, 2021 by the European Patent Office in connection with European Patent Application No. 17919096.2.
Gao, C. et. al. "Silencing pancreatic adenocarcinoma unregulated factor (PAUF) increases the sensitivity of pancreatic cancer cells to gemcitabine." Tumor Biology. Dec. 18, 2015, vol. 37, No. 6, pp. 7555-7564.
Hochnadel, I. et al. "Cancer vaccines and immunotherapeutic approaches in hepatobiliary and pancreatic cancers." Human Vaccines & Immunotherapeutics. Nov. 7, 2017, vol. 13, No. 12, pp. 2931-2952.
Kim, S. J. et al. "A PAUF-neutralizing antibody targets both carcinoma and endothelial cells to impede pancreatic tumor progression and metastasis." Biochemical and Biophysical Research Communications. Nov. 1, 2014, vol. 454, No. 1, pp. 144-150.
Song, J. et al. "Pancreatic adenocarcinoma up-regulated factor (PAUF) enhances the accumulation and functional activity of myeloid-derived suppressor cells (MDSCs) in pancreatic cancer." Oncotarget. Aug. 9, 2016, vol. 7, No. 32, pp. 51840-51853.
Written Opinion dated Oct. 27, 2020 by the Intellectual Property Office of Singapore in connection with Singaporean Patent Application No. 11201903573R.

* cited by examiner

*Primary Examiner* — Brad Duffy
*Assistant Examiner* — Cheom-Gil Cheong
(74) *Attorney, Agent, or Firm* — John P. White

(57) ABSTRACT

The present invention provides antibodies which specifically bind to pancreatic adenocarcinoma upregulated factor (PAUF) protein and uses thereof.

21 Claims, 12 Drawing Sheets

Specification includes a Sequence Listing.

| Legend | Antibody | $K_d$ ($10^{-9}$ M) |
|---|---|---|
|  | cPMAb22 | 0.01 |
|  | cPMAb205 | 0.03 |
|  | PMAb83 | 0.18 |

▶ Yield

1 : 2H2-V$_H$1-V$_L$1 : 165.5 mg/L

2 : 2H2-V$_H$1-V$_L$2 : 28.25 mg/L

3 : 2H2-V$_H$1-V$_L$3 : 42.0 mg/L

ANTIBODY SPECIFICALLY BINDING TO PAUF PROTEIN AND USE THEREOF

CROSS-REFERENCE TO RELATED APPLICATIONS

This application is a § 371 national stage of PCT International Application No. PCT/KR2017/008893, filed Aug. 16, 2017, claiming priority of Korean Patent Application No. KR 10-2017-0096370, filed Jul. 28, 2017, the contents of each of which are hereby incorporated by reference into the application.

REFERENCE TO A SEQUENCE LISTING

This application incorporates-by-reference nucleotide and/or amino acid sequences which are present, in the file named "191112_90953_Substitute_Sequence_Listing_BI.txt", which is 15.4 kilobytes in size, and which was created Nov. 12, 2019 in the IBM-PC machine format, having an operating system compatibility with MS-Windows, which is contained in the text file which is being submitted as part of this application.

TECHNICAL FIELD

The present invention relates to an antibody that specifically binds to a pancreatic adenocarcinoma upregulated factor (PAUF) protein and use thereof.

BACKGROUND ART

Anticancer drugs currently in clinical use may be classified as chemotherapeutic agents and biotherapeutic agents. Chemotherapeutic agents that were actively developed in the past are drugs that show toxicity to cancer cells. However, these drugs have problems in that they are toxic to normal cells as well as cancer cells, and are also subject to tolerance. Therefore, there are limitations to the development and use of these drugs. As such, in recent years, biotherapeutic agents that can recover or increase the immune function of the human body and thereby weaken the activity of cancer cells are being actively developed as an alternative. Examples of biotherapeutic agents which are currently in use or under development include cytokines, recombinant antibodies (e.g., monoclonal antibodies), nucleic acid molecule therapeutics, angiogenesis inhibitors, etc.

Among the biotherapeutic agents, monoclonal antibodies for treatment are characterized by having low side effects due to their high reaction specificity to targets. Antibodies exhibit therapeutic effects through various mechanisms; for example, they may specifically bind to the corresponding antigens to inhibit signal transduction or induce apoptosis by cross-linking, and additionally, may exhibit therapeutic effects by activating the immune system in vivo. Accordingly, monoclonal antibodies as an anticancer agent can specifically track cancer cells and inhibit their activity, as well as induce immune responses, and can thereby effectively remove cancer cells. As a result, treatment using monoclonal antibodies is becoming a mainstream cancer treatment. In this regard, monoclonal antibodies such as ramucirumab, rituximab, trastuzumab, etc. have been developed and used in the treatment of stomach cancer, breast cancer, liver cancer, etc.

Meanwhile, pancreatic adenocarcinoma upregulated factor (PAUF) proteins, which are overexpressed in cancer cells such as pancreatic cancer, ovarian cancer, colon cancer, uterine cervical cancer, etc. and involved in the development and metastasis of tumors, are known to upregulate and stabilize β-catenin through a new pattern of phosphorylation, thereby contributing to rapid proliferation of pancreatic cancer cells (*Experimental & Molecular Medicine*, 2011, 43, 82 to 90). Additionally, since it has been reported that small-interfering RNAs targeting PAUF proteins can reduce migration, invasion, and tumorigenic ability of pancreatic cancer cells, there is a growing interest in PAUF proteins as targets for diagnosis, treatment, etc. of cancer (*Cancer Sci.*, 2009 May, 100(5): 828 to 836; *Biochem Biophys Res Commun.* 2014 November, 454(1): 144 to 150). In this regard, a composition for diagnosis and treatment of pancreatic cancer containing an anti-PAUF protein human antibody was previously developed (KR Patent No. 10-1098186). However, there is still a need for the development of antibodies having excellent effects on diagnosis and treatment of various kinds of cancer while simultaneously improving the binding ability and affinity for PAUF proteins.

Technical Problem

The present inventors have made efforts to develop an antibody which can specifically bind to a PAUF protein and exhibit excellent effects on treatment and diagnosis of various kinds of cancer. As a result, they have developed chimeric and humanized antibodies based on anti-PAUF mouse antibodies, and have confirmed that these antibodies have higher affinity and specificity for PAUF proteins and higher anticancer activity against pancreatic cancer, ovarian cancer, etc. compared to existing anti-PAUF human antibodies, thereby completing the present invention.

Technical Solution

An object of the present invention is to provide an antibody which binds to a pancreatic adenocarcinoma upregulated factor (PAUF) protein.

Another object of the present invention is to provide a polynucleotide which encodes the antibody.

Still another object of the present invention is to provide an expression vector which contains the polynucleotide.

Still another object of the present invention is to provide a transformant in which the expression vector is introduced.

Still another object of the present invention is to provide a pharmaceutical composition for preventing or treating cancer containing the antibody.

Still another object of the present invention is to provide a method for preventing or treating cancer which includes administering the antibody to a subject.

Still another object of the present invention is to provide a method for inhibiting the proliferation, migration, or invasion of cancer cells which includes administering the antibody to a subject.

Still another object of the present invention is to provide an antibody-drug conjugate in which a drug is conjugated to the antibody.

Still another object of the present invention is to provide a cancer diagnostic composition containing the antibody.

Still another object of the present invention is to provide a cancer diagnostic kit containing the composition.

Still another object of the present invention is to provide a cancer diagnostic method, which includes detecting a PAUF protein in a biological sample isolated from a subject suspected of cancer through an antigen-antibody reaction using the antibody.

Still another object of the present invention is to provide a method for screening materials for preventing or treating cancer, which includes: (a) treating cancer cells with a candidate material for preventing or treating cancer; (b) measuring the level of PAUF proteins in the cancer cells, in which the candidate material was treated, using the antibody; and (c) determining whether the candidate material, which was treated in step (a), can be used as a material for preventing or treating cancer, when the level of the PAUF protein in step (b) is lower than that of the cancer cells not treated with the candidate material.

Advantageous Effects of the Invention

The present invention relates to an antibody specifically binding to a pancreatic adenocarcinoma upregulated factor (PAUF) protein and use thereof.

The antibody of the present invention binds to a PAUF protein with high specificity and affinity and thereby inhibits the proliferation, migration, invasion, and in vivo growth, and thus the antibody of the present invention can be effectively used in the field of diagnosis and treatment of diseases such as cancer in which a PAUF protein is overexpressed.

DETAILED DESCRIPTION OF THE INVENTION

Figure 1:
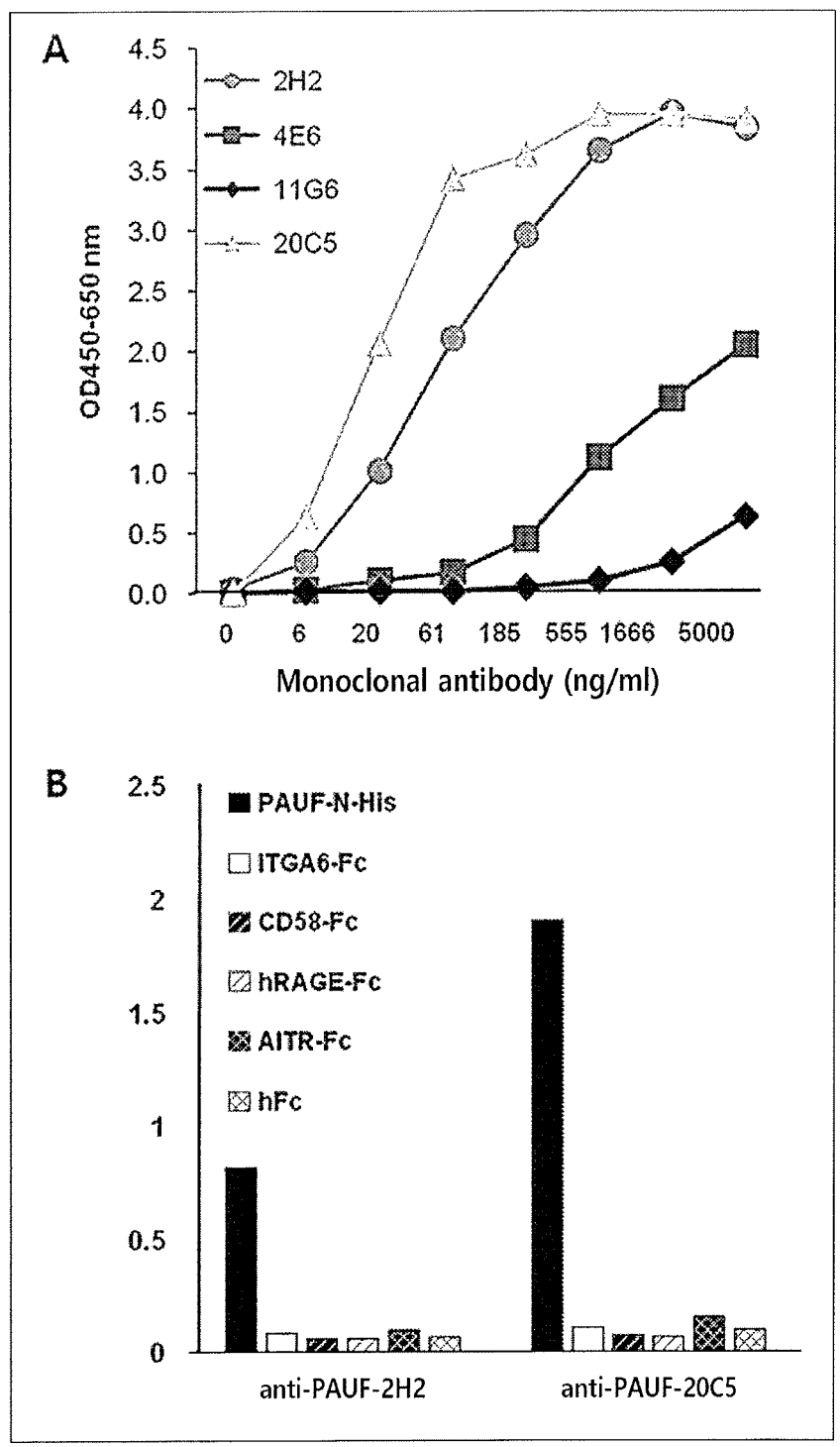
FIG. 1 shows graphs illustrating the affinity (A) and specificity (B) of 2112 and 20C5, which are anti-PAUF protein mouse antibodies, for PAUF proteins.

To achieve the above objects, an aspect of the present invention provides an antibody that binds to a pancreatic adenocarcinoma upregulated factor (PAUF) protein.

In the present invention, the inventors have developed antibodies, each of which includes a heavy chain variable region that includes a heavy chain CDR1 of SEQ ID NO: 1, a heavy chain CDR2 of SEQ ID NO: 2 or 39, and a heavy chain CDR3 of SEQ ID NO: 3, 4, or 30; and a light chain variable region that includes a light chain CDR1 of SEQ ID NO: 5, a light chain CDR2 of SEQ ID NO: 6, and a light chain CDR3 of SEQ ID NO: 7 or 31. It was confirmed that these antibodies exhibit significantly higher affinity and specificity for the PAUF proteins compared to the conventional PAUF antibodies, inhibit the proliferation, migration, and invasion of various cancers such as pancreatic cancer, ovarian cancer, etc., and inhibit in vivo growth of cancer.

As used herein, the term "pancreatic adenocarcinoma upregulated factor (PAUF) protein" refers to a protein involved in the development and metastasis of tumor. It has been reported that PAUF proteins are overexpressed in cancer cells such as pancreatic cancer, ovarian cancer, colon cancer, uterine cervical cancer, etc., and thus these proteins can be a target for diagnosis, treatment, etc. of cancer (*Cancer Sci*. 2009 May, 100(5): 828 to 36; *Biochem Biophys Res Commun*. 2014 November, 454(1): 144 to 50.).

As used herein, the term "antibody" refers to a protein molecule that acts as a receptor capable of specifically recognizing antigens, and it includes an immunoglobulin molecule that is immunologically reactive with a particular antigen. Antibodies of the present invention may include all of polyclonal antibodies, monoclonal antibodies, whole antibodies, and antibody fragments, and also chimeric antibodies and bivalent or bispecific molecules (e.g., bispecific antibodies), diabodies, triabodies, and tetrabodies. Additionally, the antibodies of the present invention include a single-chain antibody having a binding function to neonatal Fc receptors (FcRn), scabs, derivatives of an antibody constant region, and artificial antibodies based on a protein scaffold.

The whole antibody has a structure with two full-length light chains and two full-length heavy chains, in which each light chain is linked to a heavy chain by a disulfide bond. The whole antibody includes IgA, IgD, IgE, IgM, and IgG, in which IgG includes IgG1, IgG2, IgG3, and IgG4 as subtypes.

The antibody fragment refers to a fragment having an antigen-binding function and it includes Fc, Fd, Fab, Fab', Fv, F(ab')2, etc. The Fc refers to the tail portion of an antibody that interacts with a cell surface receptor called an Fc receptor. The Fd refers to the heavy chain portion included in the Fab fragment, and F(ab')2 refers to a fragment including Fd, Fab, Fab', and Fv. The Fab has a structure composed of variable regions of the light and heavy chains, a constant region of the light chain, and the first constant region of the heavy chain (CH1 domain), and the Fab has one antigen-binding site. Fab' differs from Fab in that it has a hinge region including at least one cysteine residue at the C-terminus of the heavy chain CH1 domain. The F(ab')2 antibody is produced as the cysteine residue in the hinge region of the Fab' forms a disulfide bond. A variable fragment (Fv) refers to a minimum fragment having only a heavy chain variable region and a light chain variable chain. The disulfide-stabilized Fv (dsFv) antibody fragment is characterized in that the heavy chain variable region and the light chain variable region are linked by a disulfide bond, whereas a single-chain Fv (scFv) is generally characterized in that the heavy chain variable region and the light chain variable region are linked by a covalent bond through a peptide linker. These antibody fragments can be obtained using a protease (e.g., Fab can be obtained by restriction digestion of full length antibodies with papain, and F(ab')2 fragment can be obtained by digesting With pepsin), and preferably, may be prepared through genetic recombination technology.

Generally, an immunoglobulin has a heavy chain and a light chain, and each of the heavy chain and the light chain includes a constant region and a variable region. The variable regions of the light chain and the heavy chain include three hypervariable regions called complementarity-determining regions (hereinafter, "CDR") and four framework regions (hereinafter, "FR"). The CDR of each chain mostly has the role of binding to an epitope of an antigen and it is typically called CDR1, CDR2, and CDR3 sequentially starting from the N-terminus. Additionally, the FR of each chain may be called FR1, FR2, FR3, and FR4 sequentially starting from the N-terminus.

In the present invention, the variable region of the heavy chain may be called "$V_H$"; the variable region of the light chain may be called "$V_L$"; the CDR of the heavy chain may be called "$V_H$-CDR1", "$V_H$-CDR2", and "$V_H$-CDR3"; the CDR of the light chain may be called "$V_L$-CDR1", "$V_L$-CDR2", and "$V_L$-CDR3"; the FR of the heavy chain may be called "$V_H$-FR1", "$V_H$-FR2", "$V_H$-FR3", and "$V_H$-FR4"; and the FR of the light chain may be called "$V_L$-FR1", "$V_L$-FR2", "$V_L$-FR3", and "$V_L$-FR4".

Additionally, when the antibodies of the present invention include a constant region, they may include constant regions derived from IgG, IgA, IgD, IgE, and IgM, or a combination thereof, or a hybrid thereof.

As used herein, the term "combination" means that a polypeptide encoding a single-chain immunoglobulin constant region of the same origin are linked to a single-chain polypeptide of different origin to form a dimer or multimer. For example, a dimer or multimer can be formed from two or more constant regions selected from the group consisting of IgG, IgA, IgD, IgE, and IgM constant regions.

As used herein, the term "hybrid" means that sequences corresponding to two or more immunoglobulin heavy chain constant regions of different origins are present in a single-chain of an immunoglobulin heavy chain constant region. For example, possible hybrid forms may be composed of one to four domains selected from the group consisting of CH1, CH2, CH3, and CH4 of IgG, IgA, IgD, IgE, and IgM.

Additionally, in the present invention, the antibodies may be of the same origin or different origin with regard to their variable regions and constant regions, and the origins of the CDR and variable regions and constant regions excluding the CDR may be the same or different.

As used herein, the term "antibody which specifically binds to a pancreatic adenocarcinoma upregulated factor (PAUF) protein" refers to an antibody which can bind to a PAUF protein and thereby inhibit the activity of the PAUF protein.

Specifically, the antibody which specifically binds to a pancreatic adenocarcinoma upregulated factor (PAUF) protein may be a mouse antibody, a chimeric antibody, or a humanized antibody.

Specifically, each of the antibodies of the present invention may include:

a heavy chain variable region, which includes a heavy chain CDR1 of SEQ ID NO: 1; a heavy chain CDR2 of SEQ ID NO: 2 or 39; and a heavy chain CDR3 of SEQ ID NO: 3, 4, or 30; and a light chain variable region, which includes a light chain CDR1 of SEQ ID NO: 5; a light chain CDR2 of SEQ ID NO: 6; and a light chain CDR3 of SEQ ID NO: 7 or 31, but the antibodies are not limited thereto.

Additionally, each of the antibodies of the present invention may include:

a heavy chain variable region which consists of the amino acid sequence of SEQ ID NO: 17, 28, or 37; and a light chain variable region which consists of the amino acid sequence of SEQ ID NO: 18, 29, or 38, but the antibodies are not limited thereto.

Additionally, each of the antibodies of the present invention may include a heavy chain variable region of the antibody, which includes:

a heavy chain framework region FR1 of SEQ ID NO: 8, 19, or 32; a heavy chain FR2 of SEQ ID NO: 9 or 20; a heavy chain FR3 of SEQ ID NO: 10, 21, or 33; and a heavy chain FR4 of SEQ ID NO: 11, 12, 22, 23, or 34; and a light chain variable region of the antibody, which includes the light chain FR1 of SEQ ID NO: 13, 24, or 35; the light chain FR2 of SEQ ID NO: 14 or 25; the light chain FR3 of SEQ ID NO: 15 or 26; and the light chain FR4 of SEQ ID NO: 16, 27, or 36, but the antibodies are not limited thereto.

In an embodiment of the present invention, each of the antibodies of the present invention having improved affinity and specificity compared to the existing PAUF antibodies may specifically include:

a heavy chain variable region, which includes a heavy chain CDR1 of SEQ ID NO: 1; a heavy chain CDR2 of SEQ ID NO: 2 or 39; and a heavy chain CDR3 of SEQ ID NO: 3; and a light chain variable region, which includes a light chain CDR1 of SEQ ID NO: 5; a light chain CDR2 of SEQ ID NO: 6; and a light chain CDR3 of SEQ ID NO: 7;

a heavy chain variable region, which includes a heavy chain CDR1 of SEQ ID NO: 1; a heavy chain CDR2 of SEQ ID NO: 2 or 39; and a heavy chain CDR3 of SEQ ID NO: 4; and a light chain variable region, which includes a light chain CDR1 of SEQ ID NO: 5; a light chain CDR2 of SEQ ID NO: 6; and a light chain CDR3 of SEQ ID NO: 7;

a heavy chain FR1 of SEQ ID NO: 8; a heavy chain FR2 of SEQ ID NO: 9; a heavy chain FR3 of SEQ ID NO: 10; and a heavy chain FR4 of SEQ ID NO: 11; and a light chain variable region of the antibody, which includes the light chain FR1 of SEQ ID NO: 13; the light chain FR2 of SEQ ID NO: 14; the light chain FR3 of SEQ ID NO: 15; and the light chain FR4 of SEQ ID NO: 16; or a heavy chain FR1 of SEQ ID NO: 8; a heavy chain FR2 of SEQ ID NO: 9; a heavy chain FR3 of SEQ ID NO: 10; and a heavy chain FR4 of SEQ ID NO: 12; and a light chain variable region of the antibody, which includes the light chain FR1 of SEQ ID NO: 13; the light chain FR2 of SEQ ID NO: 14; the light chain FR3 of SEQ ID NO: 15; and the light chain FR4 of SEQ ID NO: 16; and more specifically, a heavy chain variable region, which includes a heavy chain consisting of SEQ ID NO: 17; and a light chain variable region consisting of SEQ ID NO: 18, but the antibodies are not limited thereto.

In an embodiment of the present invention, the antibody which includes the heavy chain variable region consisting of the amino acid sequence of SEQ ID NO: 17 and the light chain variable region consisting of the amino acid sequence of SEQ ID NO: 18 was named as "2H2" or "cPMAb22".

Additionally, each of the antibodies of the present invention may specifically include:

a heavy chain variable region, which includes a heavy chain CDR1 of SEQ ID NO: 1; a heavy chain CDR2 of SEQ ID NO: 2 or 39; and a heavy chain CDR3 of SEQ ID NO: 3; and a light chain variable region, which includes a light chain CDR1 of SEQ ID NO: 5; a light chain CDR2 of SEQ ID NO: 6; and a light chain CDR3 of SEQ ID NO: 7;

a heavy chain variable region, which includes a heavy chain CDR1 of SEQ ID NO: 1; a heavy chain CDR2 of SEQ ID NO: 2 or 39; and a heavy chain CDR3 of SEQ ID NO: 4; and a light chain variable region, which includes a light chain CDR1 of SEQ ID NO: 5; a light chain CDR2 of SEQ ID NO: 6; and a light chain CDR3 of SEQ ID NO: 7;

a heavy chain FR1 of SEQ ID NO: 19; a heavy chain FR2 of SEQ ID NO: 20; a heavy chain FR3 of SEQ ID NO: 21; and a heavy chain FR4 of SEQ ID NO: 22; and a light chain variable region of the antibody, which includes the light chain FR1 of SEQ ID NO: 24; the light chain FR2 of SEQ ID NO: 25; the light chain FR3 of SEQ ID NO: 26; and the light chain FR4 of SEQ ID NO: 27; or a heavy chain FR1 of SEQ ID NO: 19; a heavy chain FR2 of SEQ ID NO: 20; a heavy chain FR3 of SEQ ID NO: 21; and a heavy chain FR4 of SEQ ID NO: 23; and a light chain variable region of the antibody, which includes the light chain FR1 of SEQ ID NO: 24; the light chain FR2 of SEQ ID NO: 25; the light chain FR3 of SEQ ID NO: 26; and the light chain FR4 of SEQ ID NO: 27; and more specifically, a heavy chain variable region, which includes a heavy chain consisting of SEQ ID NO: 28; and a light chain variable region consisting of SEQ ID NO: 29, but the antibodies are not limited thereto.

In an embodiment of the present invention, the antibody which includes the heavy chain variable region consisting of the amino acid sequence of SEQ ID NO: 28 and the light chain variable region consisting of the amino acid sequence of SEQ ID NO: 29 was named as "hPMAb22".

Additionally, each of the antibodies of the present invention may specifically include:

a heavy chain variable region, which includes a heavy chain CDR1 of SEQ ID NO: 1; a heavy chain CDR2 of SEQ ID NO: 2 or 39; and a heavy chain CDR3 of SEQ ID NO.: 30; and a light chain variable region, which includes a light chain CDR1 of SEQ ID NO: 5; a light chain CDR2 of SEQ ID NO: 6; and a light chain CDR3 of SEQ ID NO: 31; or a heavy chain FR1 of SEQ ID NO: 32; a heavy chain FR2 of SEQ ID NO: 9; a heavy chain FR3 of SEQ ID NO: 33; and a heavy chain FR4 of SEQ ID NO: 34; and a light chain variable region of the antibody, which includes the light chain FR1 of SEQ ID NO: 35; the light chain FR2 of SEQ ID NO: 14; the light chain FR3 of SEQ ID NO: 15; and the light chain FR4 of SEQ ID NO: 36; and more specifically, a heavy chain variable region, which includes a heavy chain consisting of SEQ ID NO: 37; and a light chain variable region consisting of SEQ ID NO: 38, but the antibodies are not limited thereto.

In an embodiment of the present invention, the antibody which includes the heavy chain variable region consisting of the amino acid sequence of SEQ ID NO: 37 and the light chain variable region consisting of the amino acid sequence of SEQ ID NO: 38 was named as "20C5" or "cPMAb205".

In a specific embodiment of the present invention, the inventors have developed mouse antibodies (i.e., 2H2 and 20C5) that bind to PAUF proteins, chimeric antibodies thereof (i.e., cPMAb22 and cPMAb205), and a humanized antibody thereof (i.e., hPMAb22), and they have confirmed that these antibodies can bind to PAUF proteins with higher specificity and affinity than to existing PAUF antibodies (FIGS. 1, 3, 4, and 8 to 11). Additionally, the present inventors have confirmed that these antibodies can inhibit the proliferation, migration, and invasion of cancer cells in ovarian cancer cell lines as well as in pancreatic cancer cell lines and pancreatic cancer cells derived from pancreatic cancer patients, and can also inhibit in vivo growth of pancreatic cancer. Furthermore, they have confirmed that the cancer therapeutic effects of these antibodies were similar to or better than that of PMAb83, which is an existing human antibody specific to PAUF proteins (FIGS. 5 to 7, and 13 to 16).

These results suggest that the antibodies of the present invention that bind to the PAUF proteins can be effectively used in the fields where the recognition of PAUF proteins is required, for example, in diagnosis, treatment, etc. of diseases in which PAUF proteins are overexpressed.

Another aspect of the present invention provides a polynucleotide which encodes the antibody of the present invention, an expression vector containing the polynucleotide, and a transformant in which the expression vector is introduced. In particular, the explanation of the antibody is the same as described above.

In the present invention, the expression vector containing a polynucleotide encoding the antibody may be a vector which can replicate and/or express the polynucleotide in eukaryotic or prokaryotic cells including mammalian cells (e.g., cells of humans, monkeys, rabbits, rats, hamsters, mice, etc.), plant cells, yeast cells, insect cells, and bacteria cells (e.g., *E. coli*, etc.), and preferably, may be operably linked to a suitable promoter so that the nucleotide can be expressed in a host cell and contain at least one selectable marker, but the expression vector is not particularly limited thereto. For example, the expression vector may be in a form where the polynucleotide is introduced into a phage, plasmid, cosmid, mini-chromosome, virus, retroviral vector, etc.

The expression vector containing a polynucleotide encoding the antibody may be an expression vector which contains a polynucleotide encoding a heavy chain or light chain of the antibody, or an expression vector which contains a polynucleotide encoding both a heavy chain and a light chain.

In the present invention, the transformant in which the expression vector is introduced may be a cell transformed by the introduction of the expression vector, including cells of bacteria (e.g., *E. coli, Streptomyces, Salmonella typhimurium*, etc.); yeast cells; fungal cells (e.g., *Pichia pastoris*, etc.), insect cells (e.g., *Drosophila, Spodoptera* (Sf9), etc.); animal cells (e.g., Chinese hamster ovarian cells (CHO), COS, mouse myeloma (NSO), 293T, bow melanoma cells, HT-1080, baby hamster kidney cells (BHK), human embryonic kidney cells (HEK), PERC.6 (human retinal cells), etc.); and plant cells, but the transformant is not particularly limited thereto.

As used herein, the term "introduction" refers to a method for delivering a vector containing a polynucleotide encoding the antibody to a host cell. The introduction may be achieved by methods such as calcium phosphate-DNA co-precipitation, DEAE-dextran-mediated transfection, polybrene-mediated transfection, electroporation, microinjection, liposomal fusion, lipofectamine, and protoplast fusion known in the art. Additionally, as used herein, the term "transfection" refers to the delivery of an object into cells using virus particles by means of infection. Additionally, vectors can be introduced into host cells by gene bombardment, etc. In the present invention, the term "introduction" may be used interchangeably with "transformation".

Still another aspect of the present invention provides a pharmaceutical composition for preventing or treating cancer containing the antibody.

The antibody shows extremely high affinity and specificity for the PAUF proteins overexpressed in cancer. The antibody can inhibit the proliferation, migration, and invasion of various kinds of cancer (e.g., pancreatic cancer, ovarian cancer, etc.), and in addition, can inhibit in vivo growth of cancer. Therefore, the antibody of the present invention can be effectively used in the prevention or treatment of diseases where PAUF proteins are overexpressed such as cancer. In particular, the explanation of the antibody is the same as described above.

As used herein, the term "cancer" refers to a lump that has abnormally grown due to autonomous overgrowth of the body's tissue, and it includes, without limitation, any type of cancer as long as it can be prevented or treated by the antibody of the present invention. Specific examples of the cancer may include pancreatic cancer, stomach cancer, colon cancer, biliary tract cancer, esophageal cancer, rectal cancer, oral cavity cancer, pharyngeal cancer, laryngeal cancer, lung cancer, colon cancer, breast cancer, ovarian cancer, uterine cervical cancer, endometrial cancer, prostate cancer, testicular cancer, bladder cancer, kidney cancer, liver cancer, bone cancer, connective tissue cancer, skin cancer, brain cancer, thyroid cancer, leukemia, Hodgkin's disease, lymphoma, and multiple myeloma blood cancer.

As used herein, the term "prevention" refers to any action resulting in suppression or delay of the onset of cancer by administering the above composition, and the term "treatment" refers to any action resulting in improvement or advantageous changes in symptoms of cancer by administering the above composition.

The pharmaceutical composition may further contain a pharmaceutically acceptable carrier, and the carrier may contain a non-naturally occurring carrier.

As used herein, the term "pharmaceutically acceptable carrier" refers to a carrier or diluent that neither irritates organisms nor interferes with the biological activity and properties of the compound to be administered. As the pharmaceutical carrier acceptable for compositions formulated as liquid solutions, one or more selected from saline, sterile water, Ringer's solution, buffered saline, albumin injection solution, dextrose solution, malto-dextrin solution, glycerol, ethanol, and a mixture thereof, which are suitable for sterilization and in vivo use, may be mixed for use. If necessary, other conventional additives such as an antioxidant, a buffer, a bacteriostatic agent, etc. may be added. Additionally, the pharmaceutical composition according to the present invention may be formulated into injectable formulations (e.g., aqueous solutions, suspensions, emulsions, etc.), pills, capsules, granules, and tablets, by further adding a diluent, a dispersant, a surfactant, a binder, and a lubricant.

The pharmaceutical composition may be prepared in any one formulation selected from the group consisting of tablets, pills, powders, granules, capsules, suspensions, solutions, emulsions, syrups, sterile aqueous solutions, non-aqueous solvents, suspensions, lyophilized preparations, and suppositories, and may be in various formulations for oral or parenteral administration. The formulations may be prepared using a commonly used diluent or excipient such as a filler, an extender, a binder, a humectant, a disintegrant, a surfactant, etc. Solid formulations for oral administration may include tablets, pills, powders, granules, capsules, etc., and these solid formulations may be prepared by adding at least one excipient (e.g., starch, calcium carbonate, sucrose or lactose, gelatin, etc.). Additionally, a lubricant (e.g., magnesium stearate, talc, etc.) may be used in addition to the simple excipient. Liquid formulations for oral administration may include suspensions, liquid medicines for internal use, emulsions, syrups, etc. and various excipients such as humectants, sweeteners, fragrances, and preservatives may be used, in addition to the simple diluents such as water and liquid paraffin. Formulations for parenteral administration may include sterile aqueous solutions, non-aqueous solvents, suspensions, emulsions, lyophilized preparations, suppositories, etc. Examples of the non-aqueous solvents and suspensions may include vegetable oils (e.g., propylene glycol, polyethylene glycol, and olive oil), an injectable ester (e.g., ethyl oleate), etc. Examples of the bases for suppositories may include Witepsol, macrogol, Tween 61, cacao butter, laurinum, glycerogelatin, etc.

The composition of the present invention may be administered in a pharmaceutically effective amount. As used herein, the term "pharmaceutically effective amount" refers to an amount sufficient for the treatment of diseases at a reasonable benefit/risk ratio applicable to medical treatment, and the level of the effective dose may be determined based on the factors including the kind of subject, severity of illness, age, sex, kind of disease, drug activity, drug sensitivity, administration time, administration route and dissolution rate, length of treatment, factors including drug(s) to be used simultaneously in combination, and other factors well known in the medical field. The composition of the present invention may be administered as an individual therapeutic agent, in combination with other therapeutic agents, or sequentially or simultaneously with a conventional therapeutic agent(s), and may be administered once or multiple times. It is important that the pharmaceutical composition be administered in the minimum amount that can obtain the maximum effect without adverse effects considering all of the factors described above, and the pharmaceutically effective amount can easily be determined by one of ordinary skill in the art.

In a specific embodiment of the present invention, it was confirmed that the antibody which binds to PAUF proteins with high specificity and affinity can inhibit the proliferation, migration, and invasion of cancer cells in ovarian cancer cell lines as well as in pancreatic cancer cell lines and pancreatic cancer cells derived from pancreatic cancer patients, and additionally, can inhibit in vivo growth of pancreatic cancer. Furthermore, it was confirmed that the therapeutic effect of the antibody against cancer was similar or superior to that of PMAb83 (i.e., the existing PAUF protein-specific human antibody (FIGS. 5 to 7, and 13 to 16).

These results suggest that the antibody that can bind to the PAUF protein of the present invention can be effectively used for the prevention or treatment of cancer.

Still another aspect of the present invention provides a method for preventing or treating cancer which includes administering the antibodies described above to a subject.

In particular, the explanations of the antibody, cancer, prevention, and treatment are the same as described above.

As used herein, the term "subject" includes mammals (e.g., rats, cattle, pigs, sheep, chickens, dogs, humans, etc.), birds, etc. which have developed or are at risk of developing cancer, but any subject in which cancer can be treated by administering the pharmaceutical composition of the present invention is included without limitation.

In the method for preventing or treating cancer of the present invention, the administration route and administration method for administering the composition are not particularly limited and any administration route and administration method may be used as long as the composition can reach target sites.

Specifically, the composition may be administered via various routes including oral and parenteral routes. Nonlimiting examples of the administration route may include oral, rectal, topical, intravenous, intraperitoneal, intramuscular, intraarterial, transdermal, intranasal, inhalation administration, etc. Additionally, the composition may be administered by any device capable of delivering an active agent to a target cell.

Still another aspect of the present invention provides a method for inhibiting proliferation, migration, or infiltration of cancer cells which includes administering the antibody of the present invention.

In particular, the explanations on the antibody, subject, and cancer are the same as described above.

The antibody shows extremely high affinity and specificity for a PAUF protein overexpressed in cancer. The antibody can inhibit the proliferation, migration, and invasion of various kinds of cancer (e.g., pancreatic cancer, ovarian cancer, etc.), and in addition, can inhibit in vivo growth of cancer. Therefore, the antibody of the present invention can be effectively used in the prevention or treatment of cancer cells.

Still another aspect of the present invention provides an antibody-drug conjugate in which a drug is conjugated to the antibody of the present invention.

In particular, the explanation on the antibody is the same as described above.

As used herein, the term "antibody-drug conjugate" refers to a material in the form where a drug is conjugated to an antibody using the target specificity, no toxicity during blood circulation, and pharmacokinetic merits of the antibody. Such an antibody-drug conjugate usually includes 3 kinds of constituting elements (i.e., a monoclonal antibody-a linker-a drug) and can improve the therapeutic effect of the antibody by delivering the drug to cells targeted by antibodies, particularly cancer cells.

As used herein, the term "drug" refers to a material that is directly or indirectly conjugated to an antibody to effect the treatment of a disease that is effectively targeted by the antibody. Drugs that can be conjugated to an antibody include radionuclides, drugs, lymphokines, toxins, bispecific antibodies, etc. Additionally, examples of the radionuclides may include $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, $^{186}$Re, etc., but the radionuclides are not limited thereto. Additionally, examples of the drugs or toxins may include etoposide, teniposide, adriamycin, daunomycin, carminomycin, aminopterin, dactinomycin, mitomycins, cis-platinum and cis-platinum analogs, bleomycins, esperamicins, 5-fluorouracil, melphalan, nitrogen mustard, etc., but the drugs or toxins that can be conjugated to the antibodies of the present invention are not limited thereto.

The antibody-drug conjugate may be prepared using a method for preparing various antibody-drug conjugates known in the art.

Still another aspect of the present invention provides a cancer diagnostic composition containing the antibody of the present invention.

In particular, the explanations of the antibody and cancer are the same as described above.

The cancer diagnostic composition of the present invention contains various kinds of antibodies which can specifically bind to PAUF proteins that are overexpressed in various kinds of cancer cells, and thus the cancer diagnostic composition of the present invention can be effectively used for diagnosis of diseases associated with the presence/absence of expression or expression level of PAUF proteins (e.g., cancer).

Still another aspect of the present invention provides a cancer diagnostic kit containing the composition.

In particular, the explanations of the composition and cancer are the same as described above.

The cancer diagnostic kit of the present invention may be constituted by further including a composition having one or more kinds of other components, a solution, or a device suitable for the method of analysis.

Still another aspect of the present invention provides a cancer diagnostic method, which includes detecting PAUF proteins in a biological sample isolated from a subject suspected of having cancer through an antigen-antibody reaction using the antibody of the present invention.

In particular, the explanations of the antibody, subject, and cancer are the same as described above.

Since it is known that PAUF proteins are overexpressed in various kinds of cancer cells, the antibody of the present invention that binds to a PAUF protein with high specificity and affinity can be effectively used for diagnosis of diseases associated with the presence/absence of expression or expression level of a PAUF protein (e.g., cancer).

The cancer diagnostic method can detect PAUF proteins by reacting the PAUF-specific antibody of the present invention with a biological sample isolated from a subject suspected of having cancer, followed by detecting the formation of an antigen-antibody complex, whereby cancer can be diagnosed.

Specifically, the cancer diagnostic method may be a method which includes (a) treating the antibody to a biological sample isolated from a subject suspected of having cancer and detecting PAUF proteins through an antigen-antibody reaction, and (b) comparing the level of PAUF proteins detected in (a) with that of the control group and determining the subject as a cancer patient when the level of PAUF proteins is higher than that of the control group.

As used herein, the term "biological sample" may include tissues, cells, whole blood, serum, plasma, tissue autopsy samples (brain, skin, lymph nodes, spinal cord, etc.), cell culture supernatant, ruptured eukaryotic cells, bacterial expression systems, etc., but the biological sample is not limited thereto. The presence of a PAUF protein or presence of cancer can be confirmed by reacting these biological samples, with or without manipulation, with the antibodies of the present invention.

As used herein, the term "antigen-antibody complex" refers to a conjugate between an antigen of a PAUF protein in a sample and an antibody of the present invention which recognizes the antigen. The formation of the antigen-antibody complex can be detected by any method such as a colorimetric method, an electrochemical method, a fluorimetric method, a luminometric method, a particle counting method, visual assessment, a scintillation counting method, etc. However, the methods for detecting the formation of the antigen-antibody complex are not limited thereto, but various applications are possible.

Various markers may be used to detect the antigen-antibody complex. Specific examples of the markers may include enzymes, fluorescent materials, ligands, luminescent materials, microparticles, radioisotopes, etc., but the markers are not limited thereto. In particular, examples of the enzymes that can be used as the markers for detection may include acetylcholinesterase, alkaline phosphatase, β-D-galactosidase, horseradish peroxidase, β-lactamase, etc.; examples of the fluorescent materials may include fluorescein, $Eu^{3+}$, $Eu^{3+}$ chelates, $Eu^{3+}$ cryptates, etc.; examples of the ligands may include biotin derivatives, etc.; examples of the luminescent materials may include acridinium esters, isoluminol derivatives, etc.; examples of the microparticles may include colloidal gold, colored latex, etc., and examples of the radioisotopes may include $^{57}Co$, $^{3}H$, $^{125}I$, $^{125}I$-Bonton Hunter reagent, etc.

Still another aspect of the present invention provides a method for screening materials for preventing or treating cancer, which includes (a) treating cancer cells with a candidate material for preventing or treating cancer; (b) measuring the level of a pancreatic adenocarcinoma upregulated factor (PAUF) protein in the cancer cells, in which the candidate material was treated, using the antibody of the present invention; and (c) determining whether the candidate material, which was treated in step (a), can be used as a material for preventing or treating cancer, when the level of the PAUF protein in step (b) is lower than that of the cancer cells not treated with the candidate material.

In particular, the explanations of the antibody, PAUF protein, and cancer are the same as described above.

As used herein, the term "candidate material for prevention or treatment of cancer" is a material which is expected to treat cancer, and any material capable of directly or indirectly ameliorating or improving cancer can be used without limitation. The candidate material includes all of the materials that are expected to be used for treatment such as compounds, genes, proteins, etc.

In the present invention, step (a) of treating cancer cells with a candidate material for the prevention or treatment of cancer may be performed using a method known in the art. In a specific embodiment, cancer cells may be treated with the candidate material and cultured together or the candidate material may be treated by administering it into a living organism containing cancer cells, but the method is not limited thereto and one of ordinary skill in the art will be able to use a method suitable for the object of the present invention.

Additionally, step (b) of measuring the level of a PAUF protein may be performed using any method known to one of ordinary skill in the art. In a specific embodiment, western blot, co-immunoprecipitation assay, enzyme linked immunosorbent assay (ELISA), histological immunostaining, flow cytometry analysis, etc. may be used, but the method is not limited thereto and one of ordinary skill in the art will be able to use a method suitable for the object of the present invention.

Finally, step (c) relates to determining whether the candidate material can be used as a material for the prevention or treatment of cancer, and the candidate material which can reduce the level of a PAUF protein, which is overexpressed in cancer cells and promotes the proliferation, migration, invasion, growth, etc. of cancer cells, can be used as a material for the prevention and treatment of cancer.

EXAMPLES

Hereinafter, the present invention will be described in more detail with reference to the following Examples. However, these Examples are for illustrative purposes only and the scope of the invention is not limited by these Examples.

Example 1. Discovery and Confirmation of Anti-PAUF Protein Mouse Antibody

Example 1-1. Discovery of 2H2 and 20C5

To develop an antibody targeting a PAUF protein, a mouse monoclonal antibody that binds to the PAUF protein was first used.

Specifically, an anti-PAUF protein mouse antibody was discovered in the following method. After injecting the PAUF protein into a mouse, an antibody to the PAUF protein was produced and B lymphocytes were isolated from the spleen of the mouse. The isolated lymphocytes were subjected to a high-fold dilution so that only one B lymphocyte was allowed to enter each well of a 96-well plate coated with the PAUF protein. Then, B lymphocytes binding to the PAUF protein were screened using HRP-labeled anti-mouse antibodies.

As a result, four kinds of anti-PAUF protein mouse antibodies (i.e., 2H2, 4E6, 11G6, and 20C5) were discovered, and the sequences of the variable regions of the heavy and light chains, CDR, and FR are described in Tables I and 2.

TABLE 1

Amino acid sequences of 2H2 (an anti-PAUF protein mouse antibody)

| Antibody Name | Category | Sequence | SEQ ID NO |
|---|---|---|---|
| 2H2 | Heavy Chain Variable Region ($V_H$) | QVQLKQSGAELVRPGALVKLSCKA SGFNIKDYYMHWVKQRPEQGLEWI GWIDPENGNTIYDPKFQGKASITA DTSSNTAYLQLSSLTSEDTAVYYC ARRAITTATAWFAYWGQGTLVTVS A | 17 |
| | $V_H$-CDR1 | GFNIKDYY | 1 |
| | $V_H$-CDR2 | IDPENGNT | 2 |
| | $V_H$-CDR3 | ARRAITTATAWFA | 3 |
| | $V_H$-CDR3 | ARRAITTATAWFAY | 4 |
| | $V_H$-FR1 | QVQLKQSGAELVRPGALVKLSCKA S | 8 |
| | $V_H$-FR2 | MHWVKQRPEQGLEWIGW | 9 |
| | $V_H$-FR3 | IYDPKFQGKASITADTSSNTAYLQ LSSLTSEDTAVYYC | 10 |
| | $V_H$-FR4 | YWGQGTLVTVSA | 11 |
| | $V_H$-FR4 | WGQGTLVTVSA | 12 |
| | Light Chain Variable Region ($V_L$) | DIVMTQSPSSLAVSAGEKVTMSCK SSQSLLNSRTRKNYLAWYQQKPGQ SPKLLIYWASTRESGVPDRFTGSG SGTDFTLTISSVQAEDLAVYYCKQ SYNLYTFGAGTKLELK | 18 |
| | $V_L$-CDR1 | QSLLNSRTRKNY | 5 |
| | $V_L$-CDR2 | WAS | 6 |
| | $V_L$-CDR3 | KQSYNLY | 7 |
| | $V_L$-FR1 | DIVMTQSPSSLAVSAGEKVTMSCK SS | 13 |
| | $V_L$-FR2 | LAWYQQKPGQSPKLLIY | 14 |
| | $V_L$-FR3 | TRESGVPDRFTGSGSGTDFTLTIS SVQAEDLAVYYC | 15 |
| | $V_L$-FR4 | TFGAGTKLELK | 16 |

TABLE 2

Amino acid sequences of 20C5 (an anti-PAUF protein mouse antibody)

| Antibody Name | Category | Sequence | SEQ ID NO |
|---|---|---|---|
| 20C5 | Heavy Chain Variable Region ($V_H$) | QVQLKESGAELVRPGALVKLSCKA SGFNIKDYYMHWVKQRPEQGLEWI GWIDPEHGNTIYDPKFQGKASLTA DTSSNTAYLQLSSLTSEDTAVYYC ARRGWLPAWFAYWGQGTLVTVSA | 37 |
| | $V_H$-CDR1 | GFNIKDYY | 1 |
| | $V_H$-CDR2 | IDPEHGNT | 39 |
| | $V_H$-CDR3 | ARRGWLPAWFAY | 30 |
| | $V_H$-FR1 | QVQLKESGAELVRPGALVKLSCKA S | 32 |
| | $V_H$-FR2 | MHWVKQRPEQGLEWIGW | 9 |
| | $V_H$-FR3 | IYDPKFQGKASLTADTSSNTAYLQ LSSLTSEDTAVYYC | 33 |
| | $V_H$-FR4 | WGQGTLVTVSA | 34 |
| | Light Chain Variable Region ($V_L$) | DIVMTQSPSSLAVSAGEKVTLSCK SSQSLLNSRTRKNYLAWYQQKPGQ SPKLLIYWASTRESGVPDRFTGSG SGTDFTLTISSVQAEDLAVYYCKQ SYNLYTFGGGTKLEIK | 38 |
| | $V_L$-CDR1 | QSLLNSRTRKNY | 5 |
| | $V_L$-CDR2 | WAS | 6 |
| | $V_L$-CDR3 | KQSYNLYT | 31 |
| | $V_L$-FR1 | DIVMTQSPSSLAVSAGEKVTLSCK SS | 35 |
| | $V_L$-FR2 | LAWYQQKPGQSPKLLIY | 14 |
| | $V_L$-FR3 | TRESGVPDRFTGSGSGTDFTLTIS SVQAEDLAVYYC | 15 |
| | $V_L$-FR4 | FGGGTKLEIK | 36 |

Example 1-2. Confirmation of Specificity to PAUF Protein

The antibody with the highest affinity for the PAUF protein among the four kinds of antibodies. (2H2, 4E6, 11G6, and 20C5) discovered in Example 1-1 was identified using the following method.

Specifically, the affinity of the antigen-antibody was tested using indirect ELISA. The PAUF-coated immuno-plate was treated with the four kinds of antibodies (2H2, 4E6, 11 G6, and 20C5) at different concentrations and the OD values were measured using the HRP-labeled anti-mouse antibody. In particular, as the OD value becomes higher, the affinity of the antibody for the PAUF becomes higher. Additionally, for the measurement of the nonspecific binding of an anti-PAUF mouse monoclonal antibody, which has a high affinity for PAUF, to other antigenic proteins, the immuno-plate was coated with PAUF and unspecified antigens so as to perform indirect ELISA.

As a result, as shown in FIGS. 1A and 1B, it was confirmed that the two kinds of antibodies (2H2 and 20C5) bind to the PAUF protein with a higher affinity compared to other antibodies and also that the two kinds of antibodies (2H2 and 20C5) have extremely high specificity to the PAUF protein.

Example 1-3. Confirmation of Epitopes

To confirm the epitopes of 2H2 and 20C5 discovered in, Example 1-1, it was confirmed whether these antibodies have the same epitope as 8F3, which is a PAUF-specific human monoclonal antibody disclosed in KR Patent No. 10-1098186 (i.e., PMAb83).

Specifically, biotin-labeled 2H2 competitive ELISA was performed. An immuno-plate was coated with PAUF, and then, biotin-labeled 2H2 antibodies and antibodies not labeled with biotin were added thereto at each ratio of 1:0, 1:50, 1:100, and 1:200. As the secondary antibody, epitopes were analyzed by measuring the OD value of each antibody using streptavidin-HRP. In particular, when the two antibodies have similar epitopes, the OD values decrease as the concentration of the unlabeled antibody increases, whereas when the epitopes of the two antibodies differ from each other, the OD values do not change even when the concentration of the unlabeled antibody increases.

Figure 2:
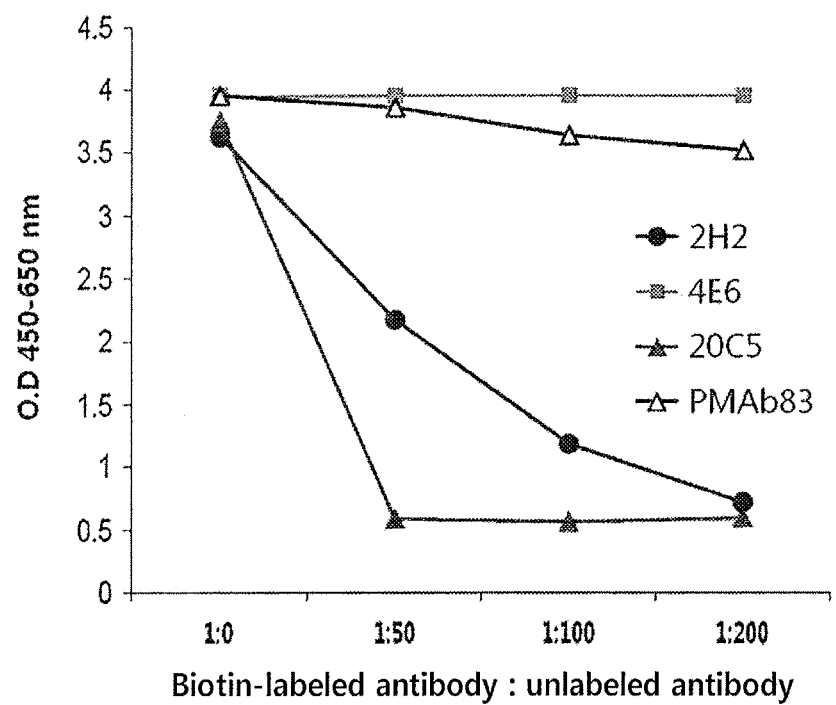
FIG. 2 shows a graph illustrating that each of 2H2 and 20C5 has an epitope different from that of PMAb83 (i.e., an existing anti-PAUF protein human antibody) and the graph shows the results of biotin-labeled 2112 competitive ELISA.

As a result, as shown in FIG. 2, it was confirmed that 2H2 or 20C5 can recognize similar epitopes and each of them has an epitope different from PMAb83.

Example 2. Preparation of Anti-PAUF Protein Chimeric Antibodies and Confirmation of their Characteristics

Example 2-1. Preparation of cPMAb22 or cPMAb205

To minimize the rejection of the mouse antibodies discovered in Example 1 (i.e., 2H2 and 20C5), chimeric antibodies were prepared in which the variable region of each antibody was retained and only the constant region thereof was replaced with a human-derived protein.

Specifically, total mRNA was isolated from hybridoma cells that produce 2H2 or 20C5 mouse antibody and each cDNA for 2H2 or 20C5 was synthesized therefrom. Then, DNA for 2H2 or 20C5 was obtained by amplifying only the heavy and light chain variable regions of each antibody through PCR. Each of the variable regions of 2H2 and 20C5 obtained through PCR was cloned into a vector having constant regions of human heavy and light chains. The 2H2 and 20C5 cloned into vectors were confirmed by DNA electrophoresis, and the sequences were analyzed and divided into groups. After removing the clones having the same sequences, the heavy and light chains of each antibody were selected. The selected sequences were expressed in HEK293 cells and thereby two kinds of chimeric antibodies having the variable region of a mouse and a constant region of humans were ultimately prepared.

As a result, cPMAb22 (i.e., a chimeric antibody of 2H2) and cPMAb205 (i.e., a chimeric antibody of 20C5) were prepared. Additionally, it was confirmed that the variable regions of heavy and the light chains, CDR, and FR sequences of these chimeric antibodies were the same as 2H2 or 20C5 described in Tables 1 and 2 above.

Example 2-2. Confirmation of Specificity to PAUF Protein

The specificity of cPMAb22 or cPMAb205 prepared in Example 2-1 to PAUF proteins was confirmed using the following method.

Specifically, indirect ELISA was performed. The chimeric antibodies (i.e., cPMAb22 and cPMAb205) and human antibody (i.e., PMAb83) were added to an immuno-plate, which was coated with the PAUF-His protein and a plurality of unspecified antigen proteins, at each concentration of 0 μg/mL, 1 μg/mL, and 5 μg/mL, and then, the OD values were measured using the anti-human kappa light chain-HRP (i.e., a secondary antibody).

Figure 3:
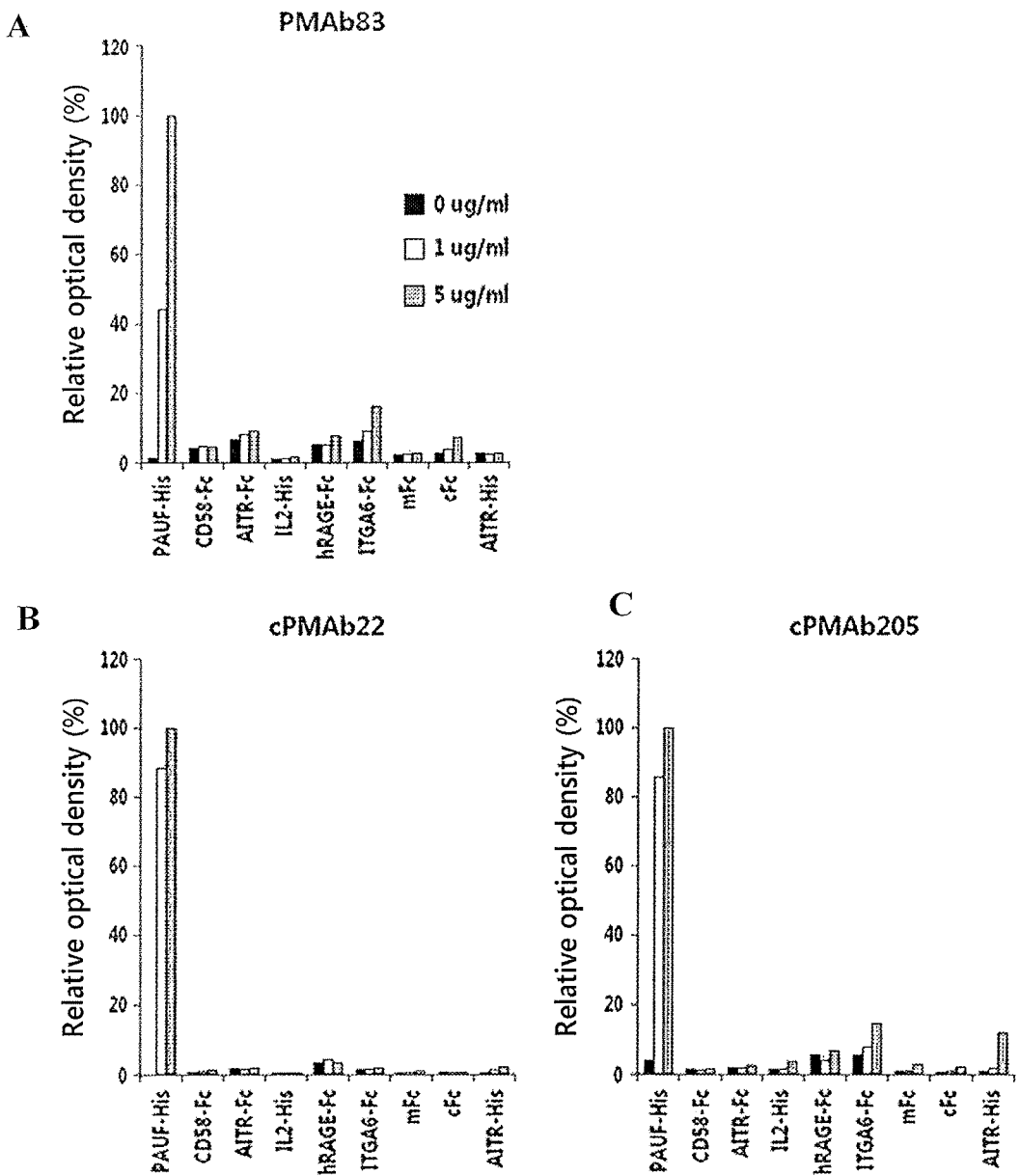
FIG. 3 shows graphs illustrating the specificity of each of cPMAb22 (B) and cPMAb205 (C), which are anti-PAUF protein chimeric antibodies, to PAUF proteins. PMAb83 (A) (i.e., a human antibody) was used as a comparative group.

As a result, as shown in FIG. 3, it was confirmed that both cPMAb22 or cPMAb205 have extremely high specificity to the PAUF protein, and in particular, have higher specificity to the PAUF proteins than PMAb83 (i.e., an existing anti-PAUF human antibody).

Example 2-3. Confirmation of Affinity for PAUF Proteins

The specificity of cPMAb22 or cPMAb205 prepared in Example 2-1 to PAUF proteins was confirmed using the following method.

Specifically, indirect ELISA was performed. An immuno-plate was coated with the PAUF-His protein and treated with each antibody at different concentrations, and the results were analyzed using the anti-human Fc-HRP capable of recognizing the constant region of human antibody as the secondary antibody. In particular, as the concentration of each antibody increases, the OD value increases.

Figure 4:
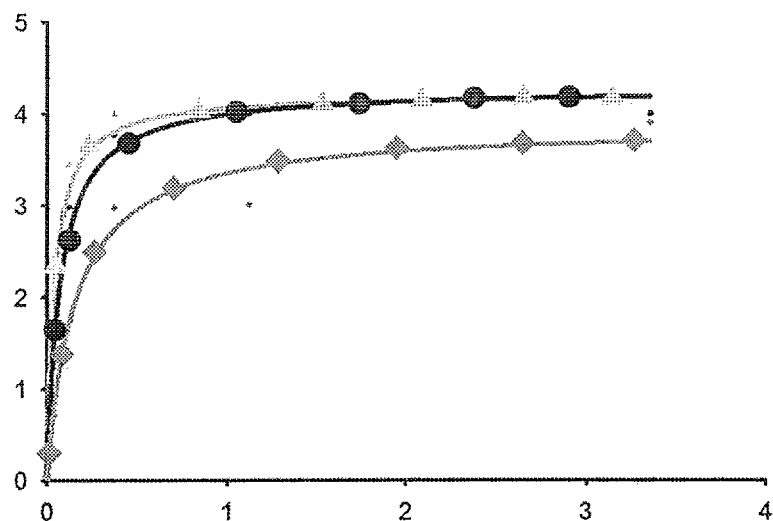
FIG. 4 shows a graph illustrating the affinity of each of cPMAb22 and cPMAb205 for PAUF proteins, based on the results of ELISA assay. PMAb83 (i.e., a human antibody) was used as a comparative group.

As a result, as shown in FIG. 4, it was confirmed that both cPMAb22 and cPMAb205 have extremely high specificity to the PAUF protein, and in particular, have higher specificity to PAUF proteins than PMAb83 (i.e., an existing anti-PAUF human antibody).

Example 2-4. Confirmation of Inhibitory Effect on Proliferation of Cancer Cells To confirm the effect of cPMAb22 (i.e., one of the chimeric antibodies prepared in Example 2-1) on cancer treatment, the inhibitory effect of cPMAb22 on the proliferation of BxPC-3 (i.e., a pancreatic cancer cell line) was confirmed.

Specifically, WST-1 proliferation assay was performed. The BxPC-3 cell line having a high self-expression level of PAUF was added to a 96-well plate at a concentration of $3 \times 10^3$ cells/well, and the 96-well plate was treated with IgG, cPMAb22 (a chimeric antibody), and PMAb83 (a human antibody) once every two days at a concentration of 15 μg/mL, respectively. Then, the 96-well plate was treated with WST-1 and the absorbance was measured at 450 nm.

Figure 5:
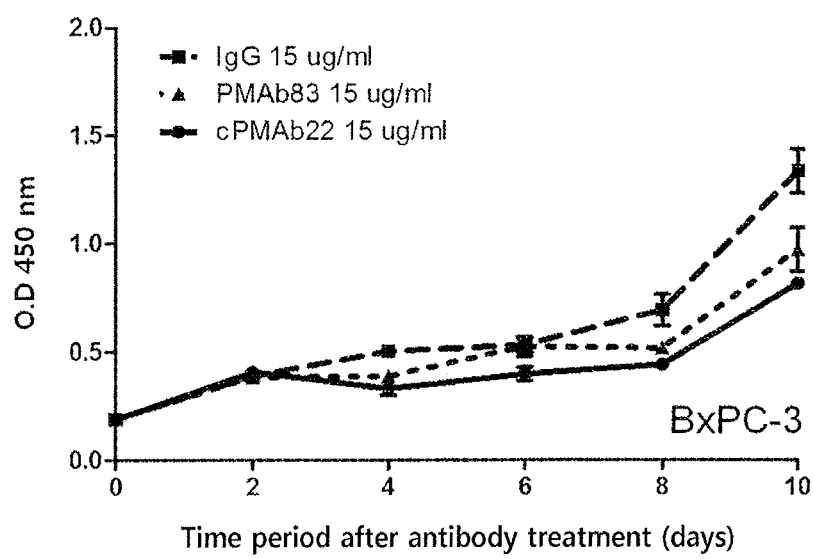
FIG. 5 shows a graph illustrating the inhibitory effect of cPMAb22 on the proliferation of cancer cells, based on the results of WST-1 proliferation assay. Specifically, the inhibitory effect of cPMAb22 on the proliferation of BxPC-3 (i.e., a pancreatic cancer cell line) was confirmed. IgG was used as the control group and PMAb83 was used as a comparative group.

As a result, as shown in FIG. 5, it was confirmed that the group treated with cPMAb22 has a higher inhibitory ability against the proliferation of BxPC-3 cells compared to the group treated with the IgG control antibody.

From the above results, it was confirmed that cPMAb22 exhibits an excellent inhibitory effect on the proliferation of cancer cells and thus cPMAb22 can be effectively used as a material for the prevention or treatment of cancer.

Example 2-5. Confirmation of Inhibitory Effect on Migration of Cancer Cells To confirm the effect of cPMAb22 (i.e., one of the chimeric antibodies prepared in Example 2-1) on cancer treatment, the inhibitory effects of cPMAb22 on the migration of CFPAC-1 (i.e., a pancreatic cancer cell line) and AMCPAC04 (i.e., pancreatic cancer cells derived from a pancreatic cancer patient) were confirmed.

Specifically, a migration assay was performed using a Transwell device. In the case of CFPAC-1 (i.e., a pancreatic cancer cell line), $5 \times 10^4$ cells were added into the upper compartment of the Transwell using a serum-free medium and then treated with IgG, cPMAb22, and PMAb83, each at a concentration of 15 μg/mL, whereas a serum-containing medium was added into the lower compartment of the transwell. After 24 hours, the migration of the cells was observed. Additionally, in the case of AMCPAC04 (i.e., pancreatic cancer cells derived from a pancreatic cancer patient), 6×10⁴ cells were added into the upper compartment of the Transwell using a serum-free medium and the cells were treated with IgG, cPMAb22, and PMAb83, each at a concentration of 10 μg/mL, whereas a serum-containing medium was added into the lower compartment of the Transwell. After 20 hours, the migration of the cells was observed.

Figure 6:
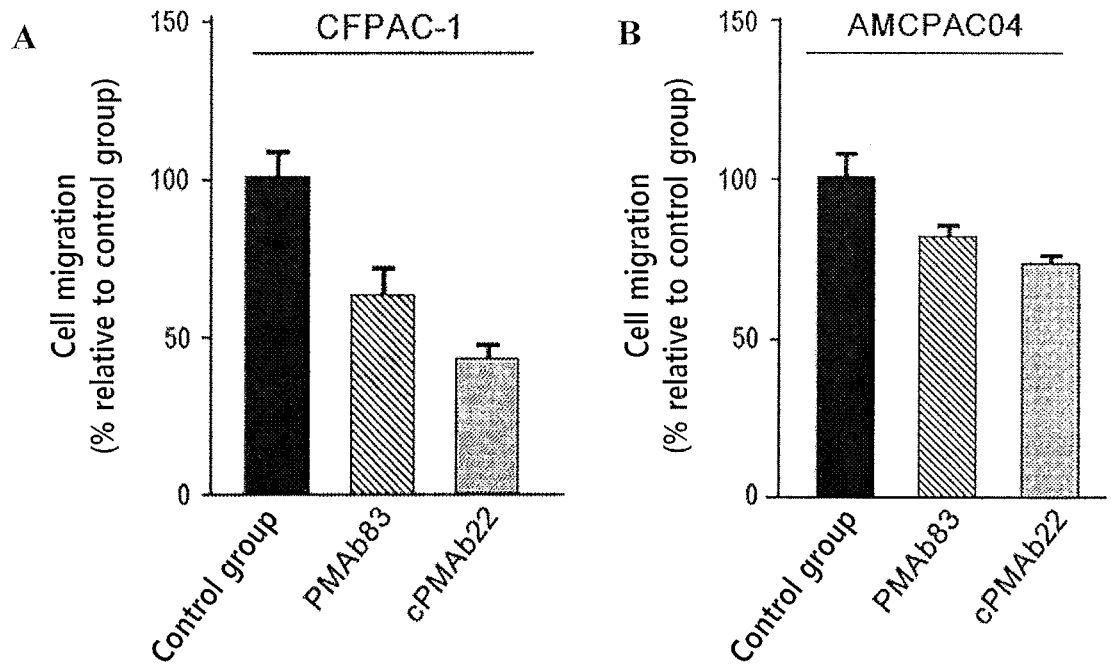
FIG. 6 shows a graph illustrating the inhibitory effect of cPMAb22 on the migration of cancer cells, based on the results of migration assay. Specifically, the inhibitory effects of cPMAb22 on CFPAC-1 (A) (i.e., a pancreatic cancer cell line) and AMCPAC04 (B) (i.e., pancreatic cancer cells derived from a pancreatic cancer patient) were confirmed. PMAb83 was used as a comparative group.

As a result, as shown in FIG. 6, it was confirmed that the group treated with cPMAb22 showed a significant decrease in the migration level of the cells from a pancreatic cancer cell line or pancreatic cancer derived from a pancreatic cancer patient, compared to the group treated with IgG (i.e., the control group antibody). In particular, it was confirmed that this migration level was even lower compared to that of the group treated with PMAb83.

From these results, it was confirmed that cPMAb22 has a superior inhibitory effect on the migration of cancer cells compared to PMAb83 (i.e., an existing anti-PAUF human antibody) and thus cPMAb22 can be effectively used as a material for the prevention or treatment of cancer.

Example 2-6. Confirmation of Inhibitory Effect on Invasion of Cancer Cells

To confirm the effect of cPMAb22 (i.e., one of the chimeric antibodies prepared in Example 2-1) on cancer treatment, the inhibitory effects of cPMAb22 on the invasion of CFPAC-1 (i.e., a pancreatic cancer cell line) and AMCPAC04 (i.e., pancreatic cancer cells derived from a pancreatic cancer patient) were confirmed.

Specifically, invasion assay was performed using a Transwell device. In particular, the Transwell was coated with Matrigel, which can artificially simulate the extracellular matrix, and the invasion ability of the pancreatic cancer cell line that changes by each antibody was observed. In the case of CFPAC-1 (i.e., a pancreatic cancer cell line), 7×10⁴ cells were added into the upper compartment of the Transwell using a serum-free medium and then treated with IgG, cPMAb22, and PMAb83, each at a concentration of 15 μg/mL, whereas a serum-containing medium was added into the lower compartment of the Transwell. After 24 hours, the invasion of the cells was observed. Additionally, in the case of AMCPAC04 (i.e., pancreatic cancer cells derived from a pancreatic cancer patient), 6×10⁴ cells were added into the upper compartment of the Transwell using a serum-free medium and the cells were treated with IgG, cPMAb22, and PMAb83, each at a concentration of 10 μg/mL, whereas a serum-containing medium was added into the lower compartment of the Transwell. After 20 hours, the invasion of the cells was observed.

Figure 7:
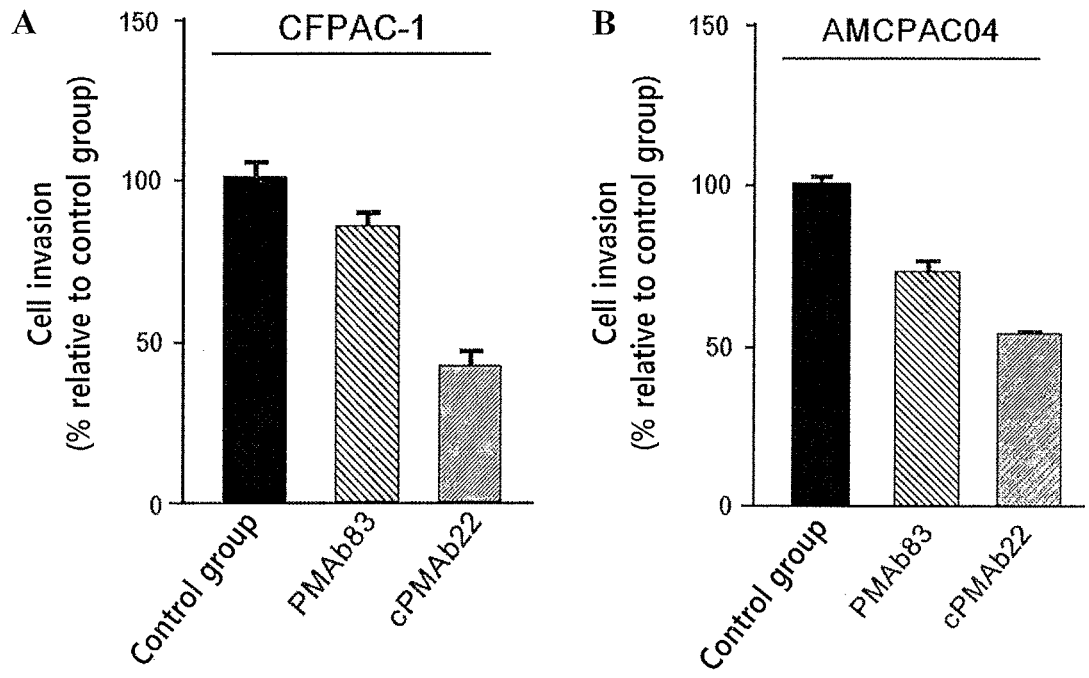
FIG. 7 shows graphs illustrating the inhibitory effect of cPMAb22 on the invasion of cancer cells, based on the results of invasion assay. Specifically, the inhibitory effects of cPMAb22 on CFPAC-1 (A) (i.e., a pancreatic cancer cell line) and AMCPAC04 (B) (i.e., pancreatic cancer cells derived from a pancreatic cancer patient) were confirmed. PMAb83 was used as a comparative group.

As a result, as shown in FIG. 7, it was confirmed that the group treated with cPMAb22 showed a significant decrease in the invasion level of the cells from a pancreatic cancer cell line or pancreatic cancer derived from a pancreatic cancer patient, compared to the group treated with IgG (i.e., the control group antibody). In particular, it was confirmed that this invasion level was even lower compared to that of the group treated with PMAb83.

From these results, it was confirmed that cPMAb22 has a superior inhibitory effect on the invasion of cancer cells compared to PMAb83 (i.e., an existing anti-PAUF human antibody) and thus cPMAb22 can be effectively used as a material for the prevention or treatment of cancer.

Example 3. Preparation of Anti-PAUF Protein Humanized Antibodies and Confirmation of their Characteristics Example 3-1. Preparation of hPMAb22

To minimize the rejection of 2H2 (i.e., the mouse antibody discovered in Example 1) and cPMAb22 (i.e., one of the chimeric antibody prepared in Example 2), humanized antibodies were prepared in which the CDRs of 21-12 and cPMAb22 (derived from a mouse) were retained while variable regions and constant regions excluding the CDRs were replaced with a human-derived protein.

Specifically, three kinds of humanized antibodies (i.e., 2H2-$V_H$1/$V_L$1, 2H2-$V_H$1/$V_L$2, and 2H2-$V_H$1/$V_L$3) were prepared through CDR grafting and their affinity and production yield were confirmed. To measure the expression levels of humanized antibodies, cross assembling was allowed between three heavy chains ($V_H$1, $V_H$2, and $V_H$3) and three light chains ($V_L$1, $V_L$2, and $V_L$3), each at a level of 5 mL, and then the resultants were transfected into HEK293 cells. Then, after 6 days, the culture solution was obtained by harvesting the medium containing the protein of the antibody and the expression rate was measured by western blotting. Additionally, the affinity of these antibodies was analyzed by indirect ELISA. Immuno-plates were coated with PAUF-His and then treated with each antibody at different concentrations. The OD values were measured using the anti-human Fc-HRP that can recognize the constant regions of human antibody as the secondary antibody.

Figure 8:
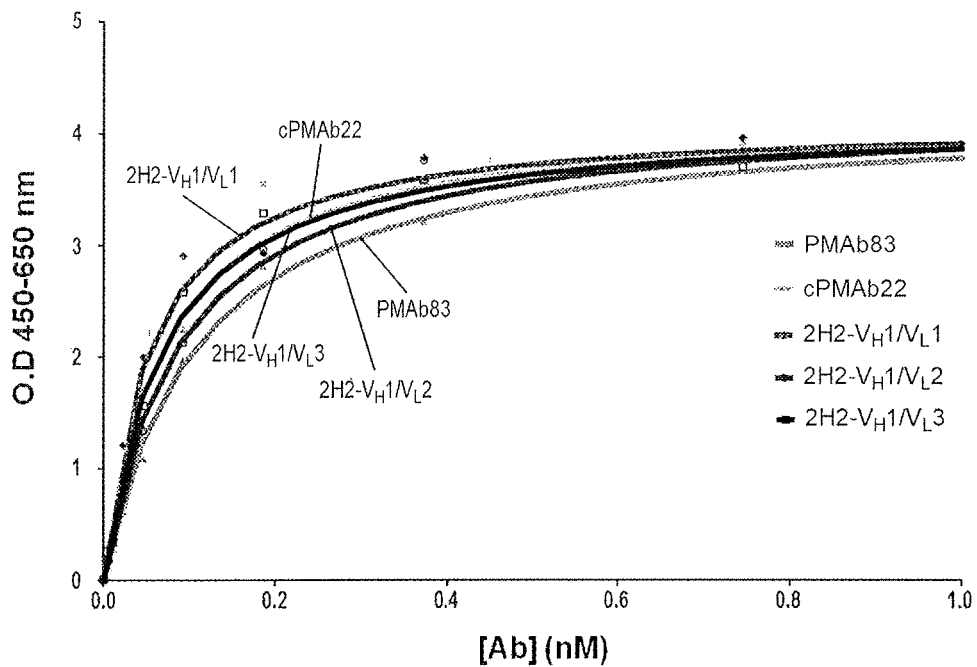
FIG. 8 shows a graph illustrating the affinity of 2H2-$V_H$1-$V_L$1, 2H2-$V_H$1-$V_L$2, and 2H2-$V_H$1-$V_L$3, which are anti-PAUF protein humanized antibodies prepared according to an embodiment of the present invention, for PAUF proteins, based on the results of ELISA assay. PMAb83, which is a human antibody, was used as a comparative group. cPMAb22 (i.e., a chimeric antibody) and PMAb83 (i.e., a human antibody) were used as comparative groups.

As a result, as shown in FIG. 8, the 2H2-$V_H$1/$V_L$1 antibody had the highest affinity for PAUF proteins compared to other humanized antibodies, thus confirming that the 2H2-$V_H$1/$V_L$1 antibody has even higher affinity compared to cPMAb22 (i.e., a chimeric antibody) or PMAb83 (i.e., an existing anti-PAUF human antibody).

Figure 9:
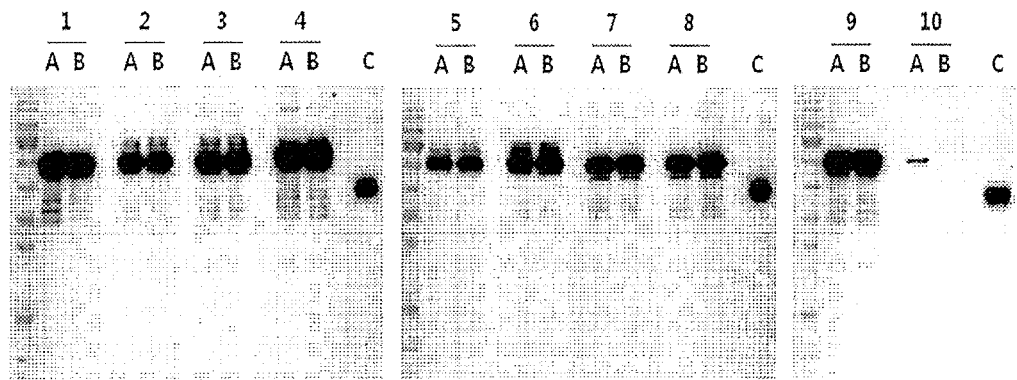
FIG. 9 shows images illustrating the production yield of the 2H2-$V_H$1-$V_L$1, 2H2-$V_H$1-$V_L$2, and 2H2-$V_H$1-$V_L$3, based on the results of western blot analysis, in which lane 1 represents 2H2-$V_H$1-$V_L$1, lane 2 represents 2H2-$V_H$1-$V_L$2, lane 3 represents 2H2-$V_H$1-$V_L$3, lane 4 represents 2H2-$V_H$2-$V_L$1, lane 5 represents 2H2-$V_H$2-$V_L$2, lane 6 represents 2H2-$V_H$2-$V_L$3, lane 7 represents 2H2-$V_H$3-$V_L$1, lane 8 represents 2H2-$V_H$3-$V_L$2, lane 9 represents 2H2-$V_H$3-$V_L$3, and lane 10 represents 2112-$V_H$4-$V_L$4, and lane A represents a protein-containing medium which was not centrifuged, lane B represents the protein-containing medium which was centrifuged to remove debris followed by filtration through a 0.22 μm filter, and lane C represents an Fc protein. The Fc protein was used as the control group.

Additionally, as shown in FIG. 9, the production yield of the 2H2-$V_H$1/$V_L$1 antibody was 165.5 mg/L, thus confirming that the 212-$V_H$1/$V_L$1 antibody has significantly higher production yield than the 2H2-$V_H$1/$V_L$1 antibody (28.25 mg/L) or the 2H2-$V_H$1/$V_L$3 antibody (42.0 mg/L).

From these results, the 2H2-$V_H$1/$V_L$1 antibody which was shown to have the highest affinity for PAUF proteins and the highest production yield was selected as the humanized antibody of 2H2 and cPMAb22 according to the present invention, assigned as "hPMAb22", and the sequences are described in Table 3 below.

TABLE 3

Amino acid sequences of hPMAb22 (i.e., an anti-PAUF protein humanized antibody)

| Antibody Name | Category | Sequence | SEQ ID NO |
|---|---|---|---|
| hPMAb22 | Heavy Chain Variable Region ($V_H$) | QVQLVQSGAEVKKPGASVKVSCKA SGFNIKDYYMHWVRQAPGQGLEWM GWIDPENGNTNYAQKFQGRVTMTR DTSISTAYMELSRLRSDDTAVYYC ARRAITTATAWFAYWGQGTLVTVS S | 28 |

TABLE 3-continued

Amino acid sequences of hPMAb22 (i.e., an anti-PAUF protein humanized antibody)

| Antibody Name | Category | Sequence | SEQ ID NO |
|---|---|---|---|
| | $V_H$-CDR1 | GFNIKDYY | 1 |
| | $V_H$-CDR2 | IDPENGNT | 2 |
| | $V_H$-CDR3 | ARRAITTATAWFA | 3 |
| | $V_H$-CDR3 | ARRAITTATAWFAY | 4 |
| | $V_H$-FR1 | QVQLVQSGAEVKKPGASVKVSCKAS | 19 |
| | $V_H$-FR2 | MHWVRQAPGQGLEWMGW | 20 |
| | $V_H$-FR3 | NYAQKFQGRVTMTRDTSISTAYMELSRLRSDDTAVYYC | 21 |
| | $V_H$-FR4 | YWGQGTLVTVSS | 22 |
| | $V_H$-FR4 | WGQGTLVTVSS | 23 |
| | Light Chain Variable Region ($V_L$) | DIVMTQSPDSLAVSLGERATINCKSSQSLLNSRTRKNYLAWYQQKPGQPPKLLIYWASTRESGVPDRFSGSGSGTDFTLTISSLQAEDVAVYYCKQSYNLYTFGQGTKVEIK | 29 |
| | $V_L$-CDR1 | QSLLNSRTRKNY | 5 |
| | $V_L$-CDR2 | WAS | 6 |
| | $V_L$-CDR3 | KQSYNLY | 7 |
| | $V_L$-FR1 | DIVMTQSPDSLAVSLGERATINCKSS | 24 |
| | $V_L$-FR2 | LAWYQQKPGQPPKLLIY | 25 |
| | $V_L$-FR3 | TRESGVPDRFSGSGSGTDFTLTISSLQAEDVAVYYC | 26 |
| | $V_L$-FR4 | TFGQGTKVEIK | 27 |

Example 3-2. Confirmation of Specificity to PAUF Proteins

The specificity of hPMAb22 (i.e., the humanized antibody prepared in Example 3-1) to PAUF proteins was confirmed using the method of Example 2-2.

Figure 10:
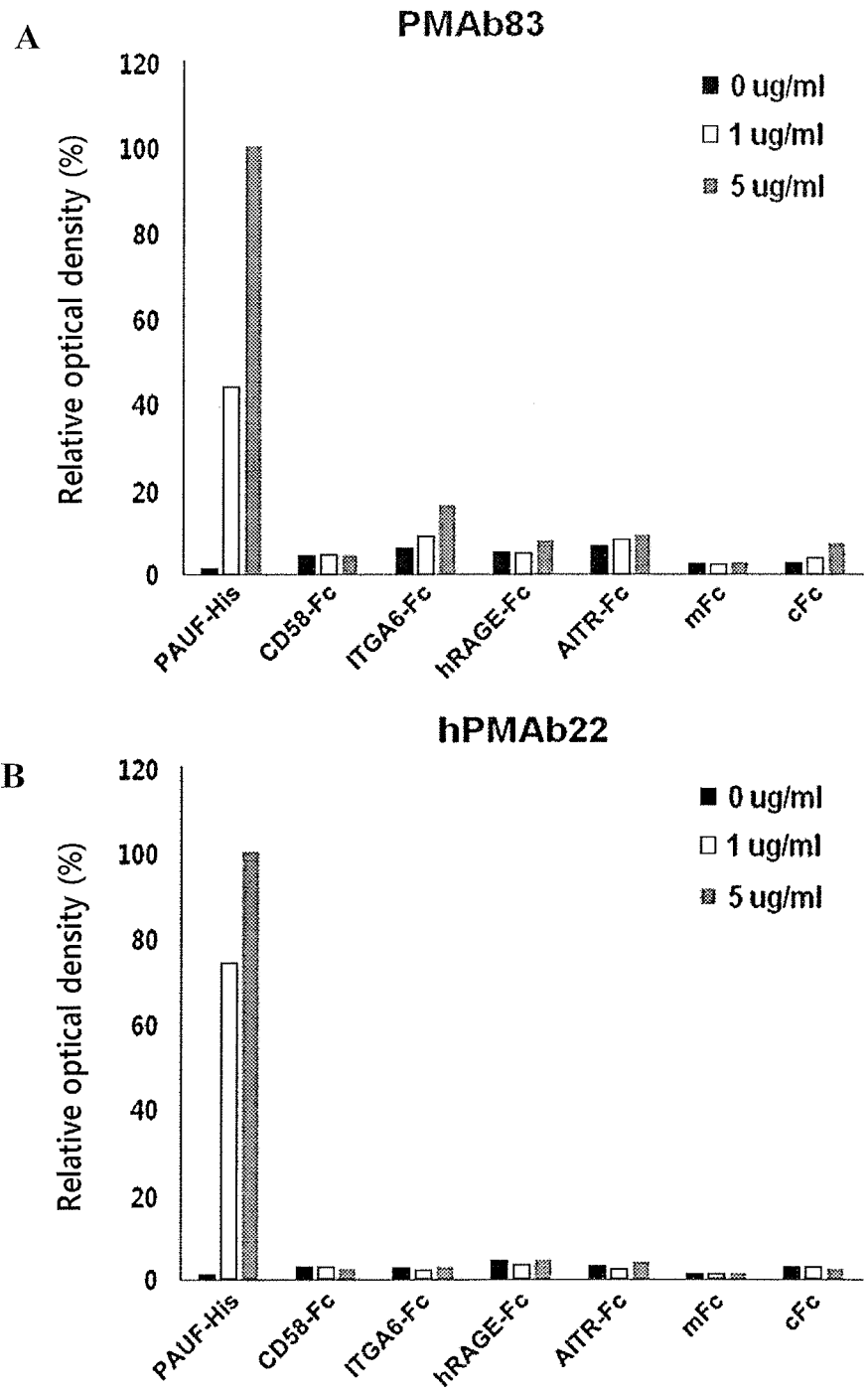
FIG. 10 shows graphs illustrating the specificity of the humanized antibody, 2H2-$V_H$1-$V_L$1 (B) (i.e., hPMAb22), to PAUF proteins. PMAb83 (A) (i.e., a human antibody) was used as a comparative group.

As a result, as shown in FIG. 10, it was confirmed that hPMAb22 has significantly high specificity to PAUF proteins, and in particular, even higher specificity than PMAb83 (i.e., an existing anti-PAUF human antibody).

Example 3-3. Confirmation of Affinity for PAUF Proteins

The affinity of hPMAb22 (i.e., the humanized antibody prepared in Example 3-1) for PAUF proteins was confirmed using the method of Example 2-2.

Specifically, the antigen-antibody binding affinity was measured using the SPR method. Antigen PAUF was immobilized on the surface of a thin metal film and the antibody was diluted at different concentrations and allowed to pass through the metal surface. The antigen-antibody binding affinity was measured by measuring the time required for binding and dissociation between antigens and antibodies.

Figure 11:
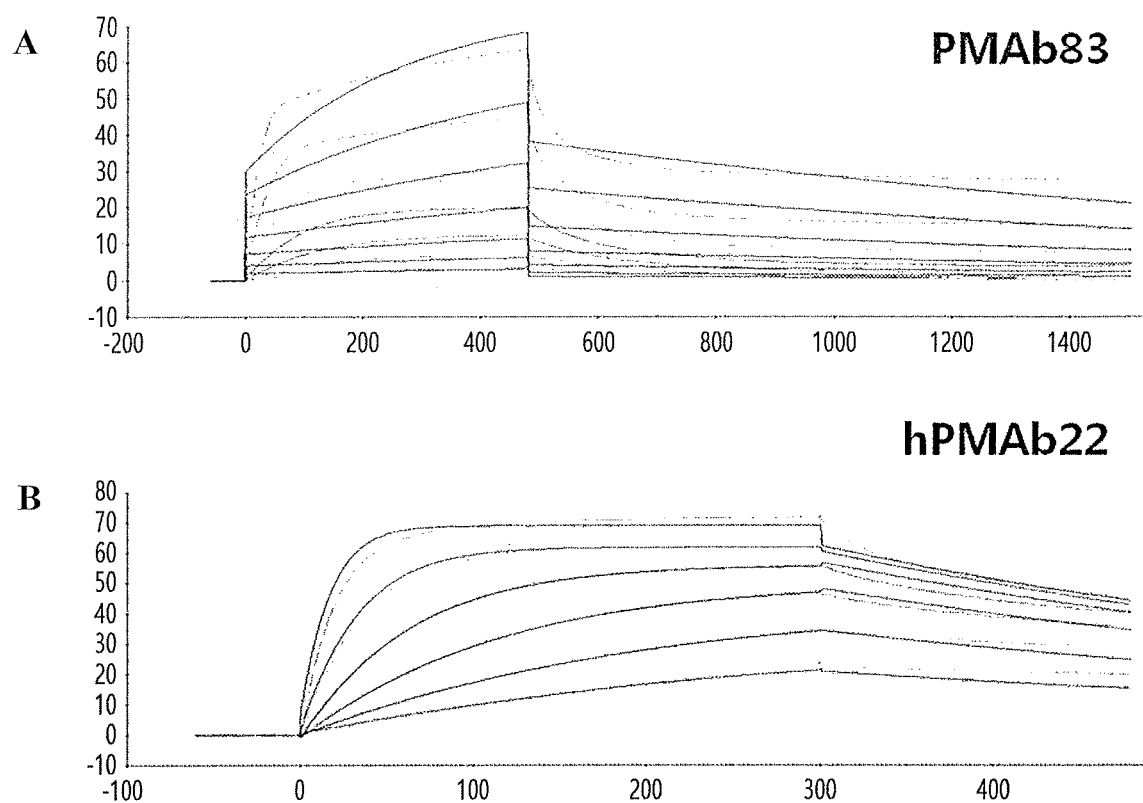
FIG. 11 shows graphs illustrating the affinity of hPMAb22 (B) for PAUF proteins, based on the results of surface plasmon resonance (SPR) analysis. PMAb83 (A) (i.e., a human antibody) was used as a comparative group.

As a result, as shown in FIG. 11, it was confirmed that PAMb83 has a $K_d$ value of $1.169 \times 10^{-9}$M and hPMAb22 has a $K_d$ value of $0.1938 \times 10^{-9}$M. From these results, it was confirmed that hPMAb22 has significantly high affinity for PAUF proteins, and in particular, higher affinity compared to PMAb83 (i.e., an existing anti-PAUF human antibody).

Example 3-4. Confirmation of Epitopes

To confirm the epitope of hPMAb22 prepared in Example 3-1, it was first confirmed whether PMAb83 (i.e., an existing anti-PAUF human antibody) and the epitope are the same according to Example 1-3.

Figure 12:
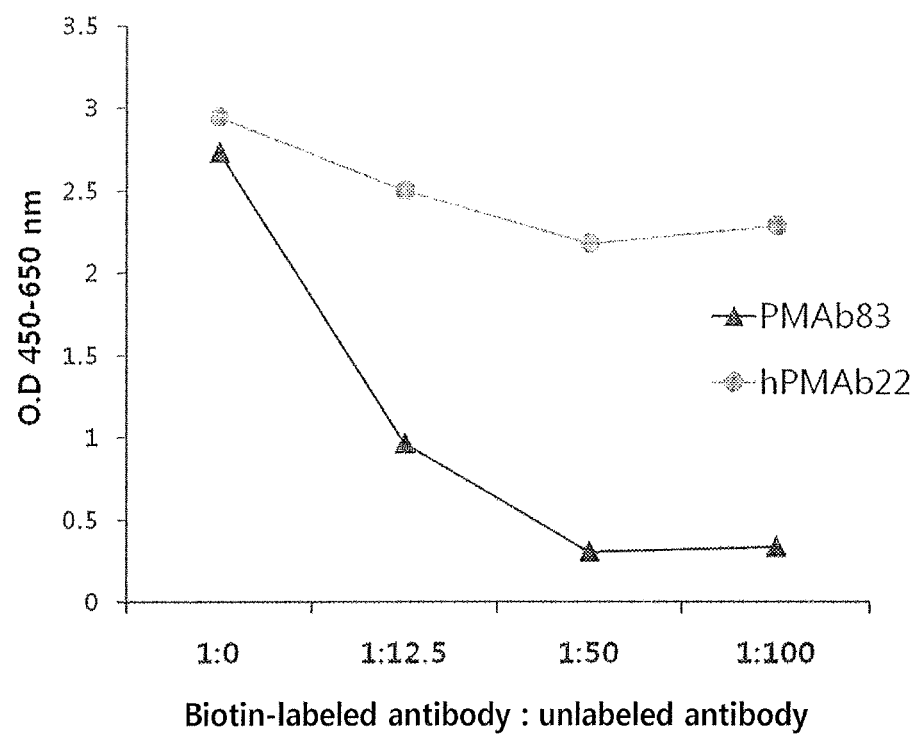
FIG. 12 shows a graph illustrating that hPMAb22 has an epitope different from that of PMAb83, which is an anti-PAUF human antibody of hPMAb22, and the graph shows the results of biotin-labeled PMAb83 competitive ELISA.

As a result, as shown in FIG. 12, it was confirmed that hPMAb22 has an epitope which is different from that of PMAb83.

Example 3-5. Confirmation of Inhibitory Effect on Proliferation of Cancer Cells To confirm the effect of hPMAb22 (i.e., the humanized antibody prepared in Example 3-1) on cancer treatment, the inhibitory effect of hPMAb22 on the proliferation of CFPAC-1 (i.e., a pancreatic cancer cell line) was confirmed by the method according to Example 2-4.

Figure 13:
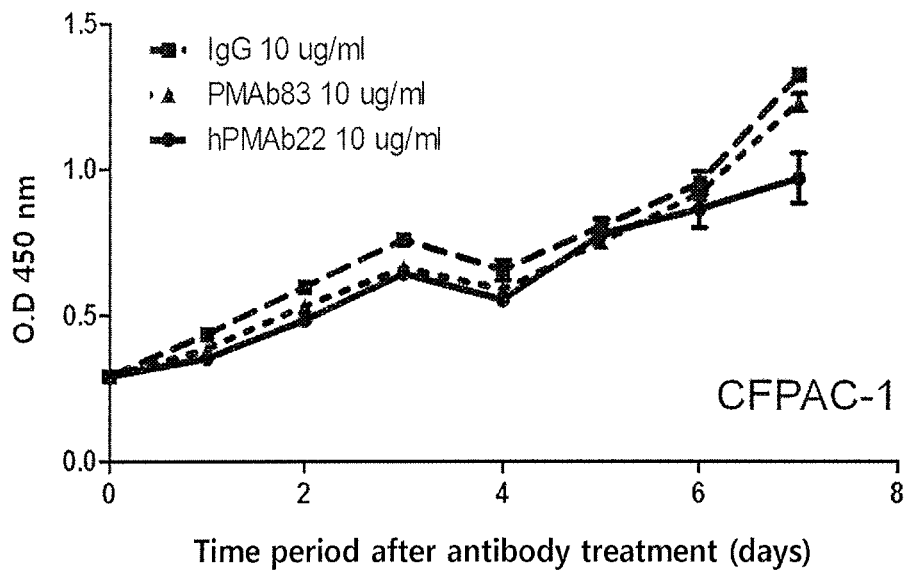
FIG. 13 shows a graph illustrating the inhibitory effect of hPMAb22 on the proliferation of cancer cells, based on the results of WST-1 proliferation assay. Specifically, the inhibitory effect of hPMAb22 on CFPAC-1 (i.e., a pancreatic cancer cell line) was confirmed. IgG was used as the control group and PMAb83 was used as a comparative group.

As a result, as shown in FIG. 13, it was confirmed that the group treated with hPMAb22 has a superior inhibitory effect on the proliferation of CFPAC-1 (i.e., a pancreatic cancer cell line), compared to the group treated with IgG (i.e., the control group antibody).

From these results, it was confirmed that hPMAb22 exhibits an excellent inhibitory effect on the proliferation of cancer cells and thus hPMAb22 can be effectively used as a material for the prevention and treatment of cancer.

Example 3-6. Confirmation of Inhibitory Effect on Migration of Cancer Cells

To confirm the effect of hPMAb22 (i.e., the humanized antibody prepared in Example 3-1) on cancer treatment, the inhibitory effect of hPMAb22 on the migration of AMCPAC06 (i.e., pancreatic cancer cells derived from a pancreatic cancer patient) and OVCAR-5 (i.e., an ovarian cancer cell line) was confirmed by the method according to Example 2-5.

Figure 14:
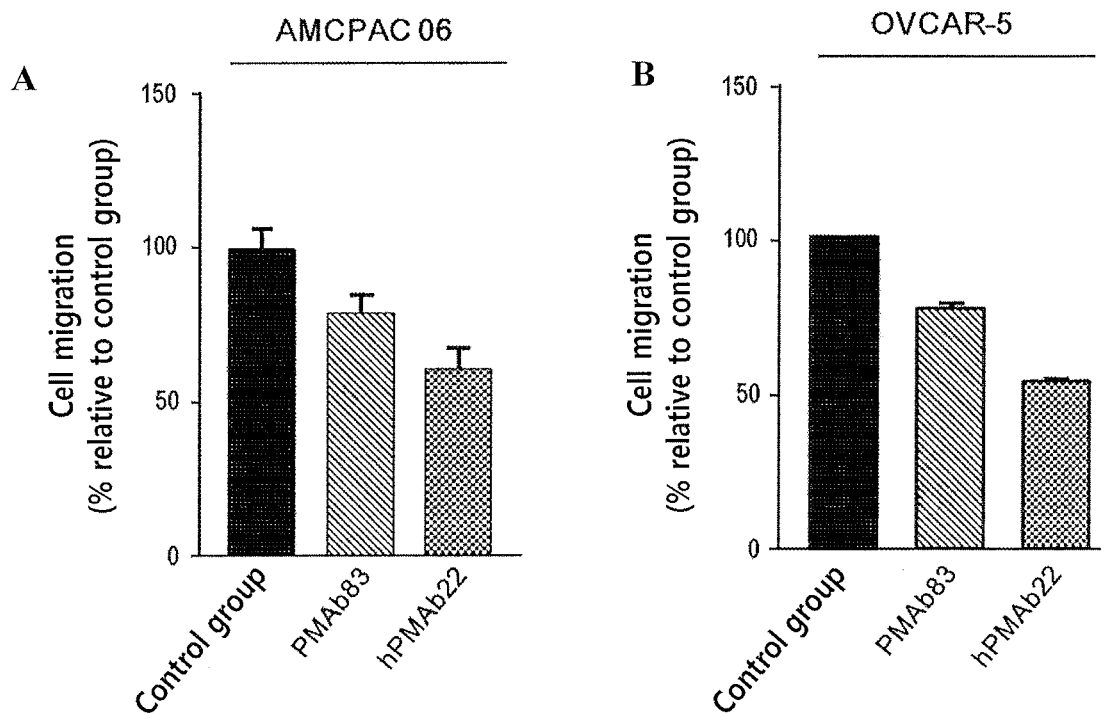
FIG. 14 shows a graph illustrating the inhibitory effect of hPMAb22 on the migration of cancer cells, based on the results of migration assay. Specifically, the inhibitory effects of hPMAb22 on AMCPAC06 (A) (i.e., pancreatic cancer cells derived from a pancreatic cancer patient) and OVCAR-5 (B) (i.e., an ovarian cancer cell line) were confirmed. PMAb83 was used as a comparative group.

As a result, as shown in FIG. 14, the group treated with hPMAb22 showed a significant decrease in the migration levels of the pancreatic cancer cell line, cancer cell line derived from a pancreatic cancer patient, and ovarian cancer cell line, compared to the group treated with IgG (i.e., the control group antibody). In particular, these results confirmed that the decrease in the migration level by the hPMAb22 treatment was even lower than that of the group treated with PMAb83.

From these results, it was confirmed that hPMAb22 exhibits a superior inhibitory effect on the migration of cancer cells compared to PMAb83 (i.e., an existing anti-PAUF human antibody) and thus hPMAb22 can be effectively used as a material for the prevention and treatment of cancer.

Example 3-7. Confirmation of Inhibitory Effect on Invasion of Cancer Cells

To confirm the effect of hPMAb22 (i.e., the humanized antibody prepared in Example 3-1) on cancer treatment, the inhibitory effect of hPMAb22 on the invasion of AMCPAC04 or AMCPAC06 (i.e., pancreatic cancer cells derived from a pancreatic cancer patient) and OVCAR-5 (i.e., an ovarian cancer cell line) was confirmed by the method according to Example 2-6.

Figure 15:
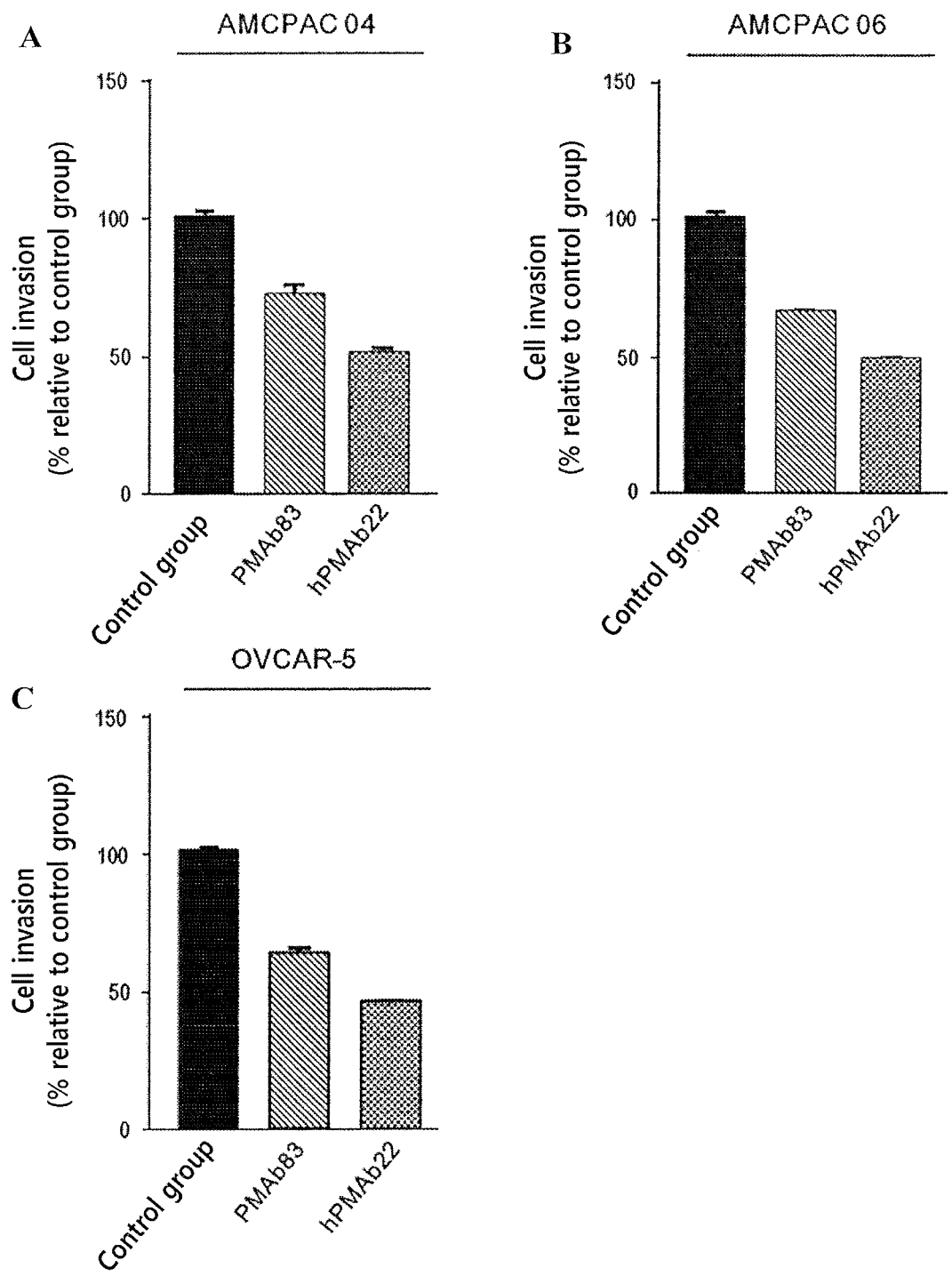
FIG. 15 shows graphs illustrating the inhibitory effect of hPMAb22 on the invasion of cancer cells, based on the results of invasion assay. Specifically, the inhibitory effects of hPMAb22 on AMCPAC04 (A) or AMCPAC06 (B) (i.e., pancreatic cancer cells derived from a pancreatic cancer patient) and OVCAR-5 (C) (i.e., an ovarian cancer cell line) were confirmed. PMAb83 was used as a comparative group.

As a result, as shown in FIG. 15, the group treated with hPMAb22 showed a significant decrease in the invasion levels of the pancreatic cancer cell line, cancer cell line derived from a pancreatic cancer patient, and ovarian cancer cell line, compared to the group treated with IgG (i.e., the control group antibody). In particular, these results confirmed that the decrease in the invasion level by the hPMAb22 treatment was even lower than that of the group treated with PMAb83.

From these results, it was confirmed that hPMAb22 exhibits a superior inhibitory effect on the invasion of cancer cells compared to PMAb83 (i.e., an existing anti-PAUF human antibody) and thus hPMAb22 can be effectively used as a material for the prevention and treatment of cancer.

Example 3-8. Confirmation of In Vivo Anticancer Effect

As hPMAb22, which is a humanized antibody specific to PAUF proteins, was confirmed to inhibit in vitro proliferation, migration, and invasion of cancer cells through Examples 3-5 to 3-7, it was examined whether hPMAb22 also exhibits the same anticancer effects in vivo.

Specifically, cancer tissue of a pancreatic ductal adenocarcinoma patient was transplanted into each NSG mouse to prepare a patient-derived xenograft (PDX) model. The cancer tissue removed from the PDX-mouse model was subcutaneously transplanted into the right leg of each nude mouse. After about 3 weeks, mice which had a tumor size of 80 $mm^3$ to 120 $mm^3$ were selected and divided into groups. The drug was administered to the tail veins of the mice. IgG and hPMAb22 were administered at a dose of 10 mg/kg twice a week for a total of 4 weeks and Gemzar® (gemcitabine), which was used as the positive control, was administered once at a dose of 50 mg/kg. In particular, the size of the tumor was measured using a caliper twice a week, and the body weight of each mouse was also measured to determine the response of the tumor to the drug. After terminating the experiment on the $31^{st}$ day, the tumors were removed and the weight of each tumor was measured and compared.

Figure 16:
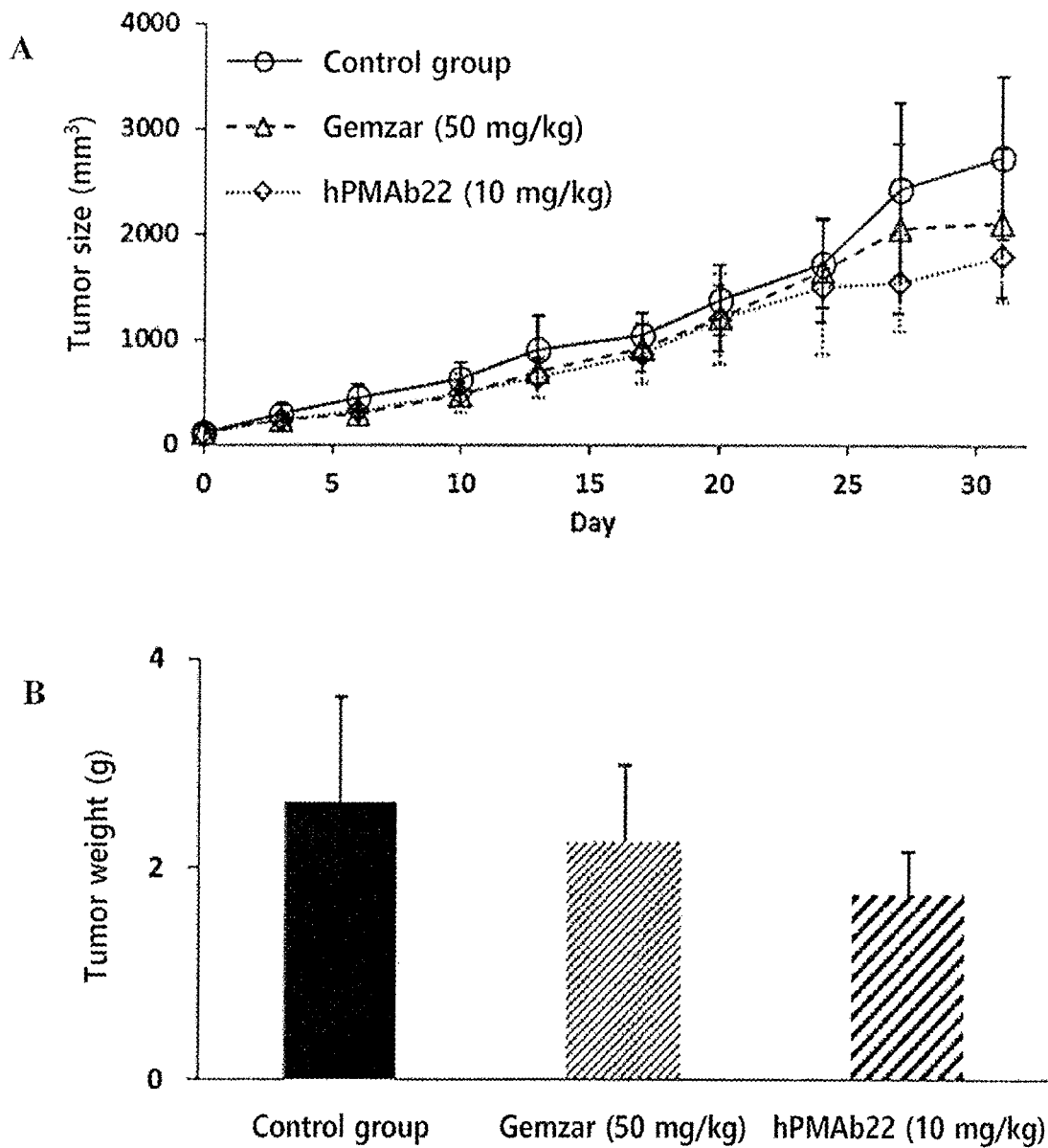
FIG. 16 shows graphs illustrating the in vivo anticancer effect of hPMAb22, and from the graphs it was confirmed that the volume (A) and weight (B) of the tumors were reduced by the administration of hPMAb22. Gemzar® (gemcitabine) was used as a comparative group.

As a result, as shown in FIG. 16, it was confirmed that the group treated with hPMAb22 showed a decrease of 30% or more in cancer cell growth compared to the group treated with the antibody of the control group. In particular, it was confirmed that the growth inhibitory effect of hPMAb22 was superior to that of the group administered with Gemzar®, being used as an anticancer agent.

From these results, it was confirmed that hPMAb22 exhibits a superior inhibitory effect on in vivo growth of cancer cells compared to Gemzar® (i.e., an existing anticancer agent) and thus hPMAb22 can be effectively used as a material for the prevention and treatment of cancer.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. An antibody which binds to a pancreatic adenocarcinoma upregulated factor (PAUF) protein, comprising:
a heavy chain variable region, which comprises a heavy chain CDR1 of SEQ ID NO: 1; a heavy chain CDR2 of SEQ ID NO: 2 or 39; and a heavy chain CDR3 of SEQ ID NO: 3, 4, or 30; and
a light chain variable region, which comprises a light chain CDR1 of SEQ ID NO: 5; a light chain CDR2 of SEQ ID NO: 6; and a light chain CDR3 of SEQ ID NO: 7 or 31.

2. The antibody of claim 1, wherein:
the heavy chain variable region of the antibody comprises a heavy chain FR1 of SEQ ID NO: 8, 19, or 32; a heavy chain FR2 of SEQ ID NO: 9 or 20; a heavy chain FR3 of SEQ ID NO: 10, 21, or 33; and a heavy chain FR4 of SEQ ID NO: 11, 12, 22, 23, or 34; and
the light chain variable region of the antibody comprises the light chain FR1 of SEQ ID NO: 13, 24, or 35; the light chain FR2 of SEQ ID NO: 14 or 25; the light chain FR3 of SEQ ID NO: 15 or 26; and the light chain FR4 of SEQ ID NO: 16, 27, or 36.

3. The antibody of claim 1, wherein:
the heavy chain variable region consists of the amino acid sequence of SEQ ID NO: 17, 28, or 37; and
the light chain variable region consists of the amino acid sequence of SEQ ID NO: 18, 29, or 38.

4. A polynucleotide encoding the antibody of claim 1.

5. An expression vector comprising the polynucleotide of claim 4.

6. A transformant, wherein the expression vector of claim 5 is introduced.

7. A pharmaceutical composition for treating cancer comprising the antibody of claim 1.

8. A method for treating cancer comprising administering the antibody of claim 1 to a subject.

9. A method for inhibiting proliferation, migration, or invasion of cancer cells comprising administering the antibody of claim 1 to a subject.

10. An antibody-drug conjugate, wherein a drug is conjugated to the antibody of claim 1.

11. A cancer diagnostic composition comprising the antibody of claim 1.

12. A cancer diagnostic kit comprising the composition of claim 11.

13. A cancer diagnostic method comprising detecting a pancreatic adenocarcinoma upregulated factor (PAUF) protein in a biological sample isolated from a subject suspected of cancer through an antigen-antibody reaction using the antibody of claim 1.

14. An in vitro and/or ex vivo method for screening materials for use in treating cancer, comprising:
(a) treating a sample of cancer cells with a candidate material for use in treating cancer;
(b) measuring the level of pancreatic adenocarcinoma upregulated factor (PAUF) protein in said sample of cancer cells using the antibody of claim 1; and
(c) determining the candidate material, with which the sample of cancer cells were treated in step (a), might be used as a material for treating cancer, when the level of PAUF protein measured in step (b) is lower than the level of PAUF protein measured in a sample of such cancer cells not treated with the candidate material,
wherein the candidate material for use in treating cancer is a material which is expected to be useful for treating cancer.

15. A polynucleotide encoding the antibody of claim 2.

16. A polynucleotide encoding the antibody of claim 3.

17. A pharmaceutical composition for treating cancer comprising the antibody of claim 2.

18. A pharmaceutical composition for treating cancer comprising the antibody of claim 3.

19. A cancer diagnostic method comprising detecting a pancreatic adenocarcinoma upregulated factor (PAUF) protein in a biological sample isolated from a subject suspected of cancer through an antigen-antibody reaction using the antibody of claim 2.

20. An in vitro and/or ex vivo method for screening materials for use in treating cancer, comprising:
(a) treating a sample of cancer cells with a candidate material for use in treating cancer;
(b) measuring the level of pancreatic adenocarcinoma upregulated factor (PAUF) protein in said sample of cancer cells using the antibody of claim 2; and
(c) determining the candidate material, with which the sample of cancer cells were treated in step (a), might be used as a material for treating cancer, when the level of PAUF protein measured in step (b) is lower than the level of PAUF protein measured in a sample of such cancer cells not treated with the candidate material,
wherein the candidate material for use in treating cancer is a material which is expected to be useful for treating cancer.

21. An in vitro and/or ex vivo method for screening materials for use in treating cancer, comprising:
(a) treating a sample of cancer cells with a candidate material for use in treating cancer;
(b) measuring the level of pancreatic adenocarcinoma upregulated factor (PAUF) protein in said sample of cancer cells using the antibody of claim 3; and (c) determining the candidate material, with which the sample of cancer cells were treated in step (a), might be used as a material for treating cancer, when the level of PAUF protein measured in step (b) is lower than the level of PAUF protein measured in a sample of such cancer cells not treated with the candidate material,
wherein the candidate material for use in treating cancer is a material which is expected to be useful for treating cancer.

\* \* \* \* \*

SEQUENCE LISTING

```
<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: VH-CDR1 of 2H2, 20C5 and hPMAb22

<400> SEQUENCE: 1

Gly Phe Asn Ile Lys Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: VH-CDR2 of 2H2 and hPMAb22

<400> SEQUENCE: 2

Ile Asp Pro Glu Asn Gly Asn Thr
1               5

<210> SEQ ID NO 3
<211> LENGTH: 13
<212> TYPE: PRT
<213> ORGANISM: Artificial Sequence
<220> FEATURE:
```

<223> OTHER INFORMATION: VH-CDR3 of 2H2 and hPMAb22

<400> SEQUENCE: 3

Ala Arg Arg Ala Ile Thr Thr Ala Thr Ala Trp Phe Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: VH-CDR3 of 2H2 and hPMAb22

<400> SEQUENCE: 4

Ala Arg Arg Ala Ile Thr Thr Ala Thr Ala Trp Phe Ala Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: VL-CDR1 of 2H2, 20C5 and hPMAb22

<400> SEQUENCE: 5

Gln Ser Leu Leu Asn Ser Arg Thr Arg Lys Asn Tyr
1               5                   10

<210> SEQ ID NO 6
<211> LENGTH: 3
<212> TYPE: PRT
<213> ORGANISM: Artificial Sequence
<220> FEATURE:
<223> OTHER INFORMATION: VL-CDR2 of 2H2, 20C5 and hPMAb22

<400> SEQUENCE: 6

Trp Ala Ser
1

<210> SEQ ID NO 7
<211> LENGTH: 7
<212> TYPE: PRT
<213> ORGANISM: Artificial Sequence
<220> FEATURE:
<223> OTHER INFORMATION: VL-CDR3 of 2H2 and hPMAb22

<400> SEQUENCE: 7

Lys Gln Ser Tyr Asn Leu Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: VH-FR1 of 2H2

<400> SEQUENCE: 8

Gln Val Gln Leu Lys Gln Ser Gly Ala Glu Leu Val Arg Pro Gly Ala
1               5                   10                  15
Leu Val Lys Leu Ser Cys Lys Ala Ser
            20                  25

<210> SEQ ID NO 9
<211> LENGTH: 17
<212> TYPE: PRT

<213> ORGANISM: Artificial Sequence
<220> FEATURE:
<223> OTHER INFORMATION: VH-FR2 of 2H2 and 20C5

<400> SEQUENCE: 9

Met His Trp Val Lys Gln Arg Pro Glu Gln Gly Leu Glu Trp Ile Gly
1               5                   10                  15

Trp

<210> SEQ ID NO 10
<211> LENGTH: 38
<212> TYPE: PRT
<213> ORGANISM: Artificial Sequence
<220> FEATURE:
<223> OTHER INFORMATION: VH-FR3 of 2H2

<400> SEQUENCE: 10

Ile Tyr Asp Pro Lys Phe Gln Gly Lys Ala Ser Ile Thr Ala Asp Thr
1               5                   10                  15

Ser Ser Asn Thr Ala Tyr Leu Gln Leu Ser Ser Leu Thr Ser Glu Asp
            20                  25                  30

Thr Ala Val Tyr Tyr Cys
        35

<210> SEQ ID NO 11
<211> LENGTH: 12
<212> TYPE: PRT
<213> ORGANISM: Artificial Sequence
<220> FEATURE:
<223> OTHER INFORMATION: VH-FR4 of 2H2

<400> SEQUENCE: 11

Tyr Trp Gly Gln Gly Thr Leu Val Thr Val Ser Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: VH-FR4 of 2H2

<400> SEQUENCE: 12

Trp Gly Gln Gly Thr Leu Val Thr Val Ser Ala
1               5                   10

<210> SEQ ID NO 13
<211> LENGTH: 26
<212> TYPE: PRT
<213> ORGANISM: Artificial Sequence
<220> FEATURE:
<223> OTHER INFORMATION: VL-FR1 of 2H2

<400> SEQUENCE: 13

Asp Ile Val Met Thr Gln Ser Pro Ser Ser Leu Ala Val Ser Ala Gly
1               5                   10                  15

Glu Lys Val Thr Met Ser Cys Lys Ser Ser
            20                  25

<210> SEQ ID NO 14
<211> LENGTH: 17
<212> TYPE: PRT
<213> ORGANISM: Artificial Sequence
<220> FEATURE:
<223> OTHER INFORMATION: VL-FR2 of 2H2 and 20C5

```
<400> SEQUENCE: 14

Leu Ala Trp Tyr Gln Gln Lys Pro Gly Gln Ser Pro Lys Leu Leu Ile
1               5                   10                  15

Tyr

<210> SEQ ID NO 15
<211> LENGTH: 36
<212> TYPE: PRT
<213> ORGANISM: Artificial Sequence
<220> FEATURE:
<223> OTHER INFORMATION: VL-FR3 of 2H2 and 20C5

<400> SEQUENCE: 15

Thr Arg Glu Ser Gly Val Pro Asp Arg Phe Thr Gly Ser Gly Ser Gly
1               5                   10                  15

Thr Asp Phe Thr Leu Thr Ile Ser Ser Val Gln Ala Glu Asp Leu Ala
            20                  25                  30

Val Tyr Tyr Cys
        35

<210> SEQ ID NO 16
<211> LENGTH: 11
<212> TYPE: PRT
<213> ORGANISM: Artificial Sequence
<220> FEATURE:
<223> OTHER INFORMATION: VL-FR4 of 2H2

<400> SEQUENCE: 16

Thr Phe Gly Ala Gly Thr Lys Leu Glu Leu Lys
1               5                   10

<210> SEQ ID NO 17
<211> LENGTH: 121
<212> TYPE: PRT
<213> ORGANISM: Artificial Sequence
<220> FEATURE:
<223> OTHER INFORMATION: VH of 2H2

<400> SEQUENCE: 17

Gln Val Gln Leu Lys Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Thr Ile Tyr Asp Pro Lys Phe
    50                  55                  60

Gln Gly Lys Ala Ser Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Ala Ile Thr Thr Ala Thr Ala Trp Phe Ala Tyr Trp Gly
            100                 105                 110

Gln Gly Thr Leu Val Thr Val Ser Ala
        115                 120

<210> SEQ ID NO 18
<211> LENGTH: 112
<212> TYPE: PRT
<213> ORGANISM: Artificial Sequence
```

<220> FEATURE:
<223> OTHER INFORMATION: VL of 2H2

<400> SEQUENCE: 18

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Ala Gly Thr Lys Leu Glu Leu Lys
            100                 105                 110

<210> SEQ ID NO 19
<211> LENGTH: 25
<212> TYPE: PRT
<213> ORGANISM: Artificial Sequence
<220> FEATURE:
<223> OTHER INFORMATION: VH-FR1 of hPMAb22

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 20
<211> LENGTH: 17
<212> TYPE: PRT
<213> ORGANISM: Artificial Sequence
<220> FEATURE:
<223> OTHER INFORMATION: VH-FR2 of hPMAb22

<400> SEQUENCE: 20

Met His Trp Val Arg Gln Ala Pro Gly Gln Gly Leu Glu Trp Met Gly
1               5                   10                  15

Trp

<210> SEQ ID NO 21
<211> LENGTH: 38
<212> TYPE: PRT
<213> ORGANISM: Artificial Sequence
<220> FEATURE:
<223> OTHER INFORMATION: VH-FR3 of hPMAb22

<400> SEQUENCE: 21

Asn Tyr Ala Gln Lys Phe Gln Gly Arg Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys
            35

<210> SEQ ID NO 22
<211> LENGTH: 12

```
<212> TYPE: PRT
<213> ORGANISM: Artificial Sequence
<220> FEATURE:
<223> OTHER INFORMATION: VH-FR4 of hPMAb22

<400> SEQUENCE: 22

Tyr Trp Gly Gln Gly Thr Leu Val Thr Val Ser Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: VH-FR4 of hPMAb22

<400> SEQUENCE: 23

Trp Gly Gln Gly Thr Leu Val Thr Val Ser Ser
1               5                   10

<210> SEQ ID NO 24
<211> LENGTH: 26
<212> TYPE: PRT
<213> ORGANISM: Artificial Sequence
<220> FEATURE:
<223> OTHER INFORMATION: VL-FR1 of hPMAb22

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ser Ser
            20                  25

<210> SEQ ID NO 25
<211> LENGTH: 17
<212> TYPE: PRT
<213> ORGANISM: Artificial Sequence
<220> FEATURE:
<223> OTHER INFORMATION: VL-FR2 of hPMAb22

<400> SEQUENCE: 25

Leu Ala Trp Tyr Gln Gln Lys Pro Gly Gln Pro Pro Lys Leu Leu Ile
1               5                   10                  15

Tyr

<210> SEQ ID NO 26
<211> LENGTH: 36
<212> TYPE: PRT
<213> ORGANISM: Artificial Sequence
<220> FEATURE:
<223> OTHER INFORMATION: VL-FR3 of hPMAb22

<400> SEQUENCE: 26

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 27
<211> LENGTH: 11
<212> TYPE: PRT
<213> ORGANISM: Artificial Sequence
<220> FEATURE:
```

<223> OTHER INFORMATION: VL-FR4 of hPMAb22

<400> SEQUENCE: 27

Thr Phe Gly Gln Gly Thr Lys Val Glu Ile Lys
1               5                   10

<210> SEQ ID NO 28
<211> LENGTH: 121
<212> TYPE: PRT
<213> ORGANISM: Artificial Sequence
<220> FEATURE:
<223> OTHER INFORMATION: VH of hPMAb22

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Ala Ile Thr Thr Ala Thr Ala Trp Phe Ala Tyr Trp Gly
            100                 105                 110

Gln Gly Thr Leu Val Thr Val Ser Ser
        115                 120

<210> SEQ ID NO 29
<211> LENGTH: 112
<212> TYPE: PRT
<213> ORGANISM: Artificial Sequence
<220> FEATURE:
<223> OTHER INFORMATION: VL of hPMAb22

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Val Glu Ile Lys
            100                 105                 110

<210> SEQ ID NO 30
<211> LENGTH: 12
<212> TYPE: PRT
<213> ORGANISM: Artificial Sequence
<220> FEATURE:
<223> OTHER INFORMATION: VH-CDR3 of 20C5

```
<400> SEQUENCE: 30

Ala Arg Arg Gly Trp Leu Pro Ala Trp Phe Ala Tyr
1               5                   10

<210> SEQ ID NO 31
<211> LENGTH: 8
<212> TYPE: PRT
<213> ORGANISM: Artificial Sequence
<220> FEATURE:
<223> OTHER INFORMATION: VL-CDR3 of 20C5

<400> SEQUENCE: 31

Lys Gln Ser Tyr Asn Leu Tyr Thr
1               5

<210> SEQ ID NO 32
<211> LENGTH: 25
<212> TYPE: PRT
<213> ORGANISM: Artificial Sequence
<220> FEATURE:
<223> OTHER INFORMATION: VH-FR1 of 20C5

<400> SEQUENCE: 32

Gln Val Gln Leu Lys Glu Ser Gly Ala Glu Leu Val Arg Pro Gly Ala
1               5                   10                  15

Leu Val Lys Leu Ser Cys Lys Ala Ser
            20                  25

<210> SEQ ID NO 33
<211> LENGTH: 38
<212> TYPE: PRT
<213> ORGANISM: Artificial Sequence
<220> FEATURE:
<223> OTHER INFORMATION: VH-FR3 of 20C5

<400> SEQUENCE: 33

Ile Tyr Asp Pro Lys Phe Gln Gly Lys Ala Ser Leu Thr Ala Asp Thr
1               5                   10                  15

Ser Ser Asn Thr Ala Tyr Leu Gln Leu Ser Ser Leu Thr Ser Glu Asp
            20                  25                  30

Thr Ala Val Tyr Tyr Cys
        35

<210> SEQ ID NO 34
<211> LENGTH: 11
<212> TYPE: PRT
<213> ORGANISM: Artificial Sequence
<220> FEATURE:
<223> OTHER INFORMATION: VH-FR4 of 20C5

<400> SEQUENCE: 34

Trp Gly Gln Gly Thr Leu Val Thr Val Ser Ala
1               5                   10

<210> SEQ ID NO 35
<211> LENGTH: 26
<212> TYPE: PRT
<213> ORGANISM: Artificial Sequence
<220> FEATURE:
<223> OTHER INFORMATION: VL-FR1 of 20C5

<400> SEQUENCE: 35

Asp Ile Val Met Thr Gln Ser Pro Ser Ser Leu Ala Val Ser Ala Gly
1               5                   10                  15
```

Glu Lys Val Thr Leu Ser Cys Lys Ser Ser
        20                  25

<210> SEQ ID NO 36
<211> LENGTH: 10
<212> TYPE: PRT
<213> ORGANISM: Artificial Sequence
<220> FEATURE:
<223> OTHER INFORMATION: VL-FR4 of 20C5

<400> SEQUENCE: 36

Phe Gly Gly Gly Thr Lys Leu Glu Ile Lys
1               5                   10

<210> SEQ ID NO 37
<211> LENGTH: 119
<212> TYPE: PRT
<213> ORGANISM: Artificial Sequence
<220> FEATURE:
<223> OTHER INFORMATION: VH of 20C5

<400> SEQUENCE: 37

Gln Val Gln Leu Lys Glu Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu His Gly Asn Thr Ile Tyr Asp Pro Lys Phe
    50                  55                  60

Gln Gly Lys Ala Ser Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Gly Trp Leu Pro Ala Trp Phe Ala Tyr Trp Gly Gln Gly
            100                 105                 110

Thr Leu Val Thr Val Ser Ala
        115

<210> SEQ ID NO 38
<211> LENGTH: 112
<212> TYPE: PRT
<213> ORGANISM: Artificial Sequence
<220> FEATURE:
<223> OTHER INFORMATION: VL of 20C5

<400> SEQUENCE: 38

Asp Ile Val Met Thr Gln Ser Pro Ser Ser Leu Ala Val Ser Ala Gly
1               5                   10                  15

Glu Lys Val Thr Leu Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

```
Ser Tyr Asn Leu Tyr Thr Phe Gly Gly Thr Lys Leu Glu Ile Lys
            100                 105                 110

<210> SEQ ID NO 39
<211> LENGTH: 8
<212> TYPE: PRT
<213> ORGANISM: Artificial Sequence
<220> FEATURE:
<223> OTHER INFORMATION: VH-CDR2 of 20C5

<400> SEQUENCE: 39

Ile Asp Pro Glu His Gly Asn Thr
1               5
```